US008580732B2

(12) United States Patent
Newgard et al.

(10) Patent No.: US 8,580,732 B2
(45) Date of Patent: Nov. 12, 2013

(54) PEPTIDE THERAPY FOR HYPERGLYCEMIA

(75) Inventors: Christopher B. Newgard, Durham, NC (US); Samuel B. Stephens, Durham, NC (US); Jonathan C. Schisler, Morrisville, NC (US)

(73) Assignee: Duke University, Durham, NC (US)

( * ) Notice: Subject to any disclaimer, the term of this patent is extended or adjusted under 35 U.S.C. 154(b) by 367 days.

(21) Appl. No.: 12/755,907

(22) Filed: Apr. 7, 2010

(65) Prior Publication Data

US 2010/0331247 A1 Dec. 30, 2010

Related U.S. Application Data

(60) Provisional application No. 61/167,760, filed on Apr. 8, 2009, provisional application No. 61/167,473, filed on Apr. 7, 2009.

(51) Int. Cl.
*A61K 38/00* (2006.01)
*A61P 38/28* (2006.01)
*A61P 7/12* (2006.01)

(52) U.S. Cl.
USPC .......................................................... 514/6.9

(58) Field of Classification Search
None
See application file for complete search history.

(56) References Cited

U.S. PATENT DOCUMENTS

| | | | |
|---|---|---|---|
| 3,174,901 | A | 3/1965 | Sterne |
| 4,002,531 | A | 1/1977 | Royer |
| 4,179,337 | A | 12/1979 | Davis et al. |
| 5,349,052 | A | 9/1994 | Delgado et al. |
| 5,612,460 | A | 3/1997 | Zalipsky |
| 5,643,575 | A | 7/1997 | Martinez et al. |
| 2010/0331247 | A1 | 12/2010 | Newgard et al. |

FOREIGN PATENT DOCUMENTS

| | | |
|---|---|---|
| EP | 0401384 | 3/1996 |
| WO | WO 87/05330 | 9/1987 |
| WO | WO 95/06058 | 3/1995 |
| WO | WO 98/32466 | 7/1998 |

OTHER PUBLICATIONS

Abdul-Ghani, M. A. et al., "Contributions of beta-cell dysfunction and insulin resistance to the pathogenesis of impaired glucose tolerance and impaired fasting glucose," Diabetes Care (2006) 29:1130-1139.
Ahren, B. et al., "Improved glucose tolerance and insulin secretion by inhibition of dipeptidyl peptidase IV in mice," Eur. J. Pharmacol. (2000) 404:239-245.
Altschul et al., "Basic Local Alignment Search Tool" J. Mol. Biol. (1990) 215:403-410.
Altschul et al., "Methods for assessing the statistical significance of molecular sequence features by using general scoring schemes" Proc. Natl. Acad. Sci. (1990) 87:2264-2268.
Altschul, "Applications and statistics for multiple high-scoring segments in molecular sequences" Proc. Natl. Acad. Sci. (1993) 90:5873-5877.
An, J. et al., "Hepatic expression of malonyl-CoA decarboxylase reverses muscle, liver and whole-animal insulin resistance," Nat. Med. (2004) 10:268-274.
Aplin et al., "Preparation, Properties, and Applications of Carbohydrate Conjugated of Proteins and Lipids" CRC Crit. Rev. Biochem. (1981) 22:259-306.
Bartolomucci, A. et al., "TLQP-21, a VGF-derived peptide, increases energy expenditure and prevents the early phase of diet-induced obesity," Proc. Natl. Acad. Sci. U.S.A. (2006) 103:14584-14589.
Bartolomucci, a. et al., "The role of the *vgf* gene and VGF-derived peptides in nutrition and metabolism," Genes Nutr. (2007) 2:169-180.
Butler, A. E. et al., "Beta-cell deficit and increased beta-cell apoptosis in humans with type 2 diabetes," Diabetes (2003) 52:102-110.
Clark, J. B. et al., "The diabetic Zucker fatty rat," Proc. Soc. Exp. Biol. Med. (1983) 173:68-75.
Coco, C. et al., "VGF metabolic-related gene: distribution of its derived peptides in mammalian pancreatic islets," J. Histochem. Cytochem. (2007) 55:619-628.
Creutzfeldt, W. et al., "The incretin concept today," Diabetologia (1979) 16:75-85.
Delgado et al., "The Uses and Properties of PEG-Linked Proteins" Crit. Rev. Thera. Drug Carrier Sys. (1992) 9:249-304.
Drucker, D. J. et al., "Glucagon-like peptide I stimulates insulin gene expression and increases cyclic AMP levels in a rat islet cell line," Proc. Natl. Acad. Sci. U.S.A. (1987) 84:3434-3438.
Drucker, D. J. et al., "The incretin system: glucagon-like peptide-1 receptor agonists and dipeptidyl peptidase-4 inhibitors in type 2 diabetes," Lancet (2006) 368:1696-1705.
Duckworth, W. et al., "Glucose control and vascular complications in veterans with type 2 diabetes," N. Engl. J. Med. (2009) 360:129-139.
Dupre, J. et al., "Stimulation of insulin secretion by gastric inhibitory polypeptide in man," J. Clin. Endocrinol. Metab. (1973) 37:826-828.
Efanova, I. B. et al., "Glucose and tolbutamide induce apoptosis in pancreatic beta-cells. A process dependent on intracellular Ca2+ concentration," J. Biol. Chem. (1998) 273:33501-33507.
Elliott, R. M. et al., "Glucagon-like peptide-1 (7-36) amide and glucose-dependent insulinotropic polypeptide secretion in response to nutrient ingestion in man: acute post-prandial and 24-h secretion patterns," J. Endocrinol. (1993) 138:159-166.
Ferri, G. L. et al., "A novel neuroendocrine gene product: selective VGF8a gene expression and immuno-localisation of the VGF protein in endocrine and neuronal populations," Brain Res. Mol. Brain Res. (1992) 13:139-143.
Filipsson, K. et al., "PACAP and PACAP receptors in insulin producing tissues: localization and effects," Regul. Pept. (1998) 74:167-175.
Finegood, D. T. et al., "Beta-cell mass dynamics in Zucker diabetic fatty rats. Rosiglitazone prevents the rise in net cell death," Diabetes (2001) 50:1021-1029.

(Continued)

*Primary Examiner* — Thomas Heard
(74) *Attorney, Agent, or Firm* — Michael Best & Friedrich LLP

(57) ABSTRACT

Methods of modulating blood glucose levels treating hyperglycemia and related complications and conditions by administration of a VGF biomolecule to a patient in need of such treatment are provided. Methods of enhancing insulin secretion from islet beta cells in a mammal exhibiting reduced insulin secretion by administration of a therapeutically effective amount of a VGF biomolecule are also provided.

14 Claims, 11 Drawing Sheets

(56) References Cited

OTHER PUBLICATIONS

Francis, G.E., et al., "PEGylation of cytokines and other therapeuticproteins and peptides: the importance of biological optimisation of coupling techniques," Int. J Hematology 68:1-18, Elsevier ScienceIreland Ltd. (1998).

Garcia, A. L. et al., "A prohormone convertase cleavage site within a predicted alpha-helix mediates sorting of the neuronal and endocrine polypeptide VGF into the regulated secretory pathway," J. Biol. Chem. (2005) 280:41595-41608.

Genuth, S. et al., "Follow-up report on the diagnosis of diabetes mellitus," Diabetes Care (2003) 26:3160-3167.

Gerstein, H. C. et al., "Effects of intensive glucose lowering in type 2 diabetes," N. Engl. J. Med. (2008) 358:2545-2559.

GenBank Accession No. NM_030997. Rat VGF peptide sequence, Oct. 2011.

GeneBank Acession No. BC063835. Human VGF protein sequence, Jul. 2006.

Hahm, S. et al., "Targeted deletion of the Vgf gene indicates that the encoded secretory peptide precursor plays a novel role in the regulation of energy balance," Neuron (1999) 23:537-548.

Herrmann, C. et al., "Glucagon-like peptide-1 and glucose-dependent insulin-releasing polypeptide plasma levels in response to nutrients," Digestion (1995) 56:117-126.

Holman, R. R. et al., "10-year follow-up of intensive glucose control in type 2 diabetes," N. Engl. J. Med. (2008) 359:1577-1589.

Holst, J. J. et al., "Truncated glucagon-like peptide I, an insulin-releasing hormone from the distal gut," FEBS Lett. (1987) 211:169-174.

Hunsberger, J. G., et al., "Antidepressant actions of the exercise-regulated gene VGF," Nat. Med. (2007) 13:1476-1482.

Jamen, F. et al., "Pituitary adenylate cyclase-activating polypeptide receptors mediating insulin secretion in rodent pancreatic islets are coupled to adenylate cyclase but not to PLC," Endocrinology (2002) 143:1253-1259.

Kahn, S. E. et al., "Glycemic durability of rosiglitazone, metformin, or glyburide monotherapy," N. Engl. J. Med. (2006) 355:2427-2423.

Kawai, K. et al., "Pituitary adenylate cyclase activating polypeptide stimulates insulin release from the isolated perfused rat pancreas," Life Sci. (1992) 50:257-261.

Kieffer, T. J. et al., "Degradation of glucose-dependent insulinotropic polypeptide and truncated glucagon-like peptide 1 in vitro and in vivo by dipeptidyl peptidase IV," Endocrinology (1995) 136:3585-3596.

Koves, T. R. et al., "Mitochondrial overload and incomplete fatty acid oxidation contribute to skeletal muscle insulin resistance," Cell. Metab. (2008) 7:45-56.

Kreymann, B. et al., "Glucagon-like peptide-1 7-36: a physiological incretin in man," Lancet (1987) 2:1300-1304.

Levi, A. et al., "Processing, distribution, and function of VGF, a neuronal and endocrine peptide precursor," Cell. Mol. Neurobiol. (2004) 24:517-533.

Maedler, K. et al., "Sulfonylurea induced beta-cell apoptosis in cultured human islets," J. Clin. Endocrinol. Metab. (2005) 90:501-506.

Malik et al., "Polythylene Glycol (PEG)-modified Granulocyte-Macrophage Colony-stimulating Factor (GM-CSF) with Conserved Biological Activity" Exp. Hematol. (1992) 20:1028-1035.

Mayo, K. E. et al., "International Union of Pharmacology. XXXXV. The glucagon receptor family," Pharmacol. Rev. (2003) 55:167-194.

Mentlein, R. B. et al., "Dipeptidyl-peptidase IV hydrolyses gastric inhibitory polypeptide, glucagon-like peptide-1 (7-36) amide, peptide histidine methionine and is responsible for their degradation in human serum," Eur. J. Biochem. (1993) 241:829-835.

Mojsov, S. et al., "Insulinotropin: glucagon-like peptide I (7-37) co-encoded in the glucagon gene is a potent stimulator of insulin release in the perfused rat pancreas," J. Clin. Invest. (1987) 79:616-619.

Nathan, D.M. et al., "Intensive diabetes treatment and cardiovascular disease in patients with type 1 diabetes," N. Engl. J. Med. (2005) 353:2643-2653.

Ovalle, F. et al., "Clinical evidence of thiazolidinedione-induced improvement of pancreatic beta-cell function in patients with type 2 diabetes mellitus," Diabetes Obes. Metab. (2002) 4:56-59.

Patel, A. et al., "Intensive blood glucose control and vascular outcomes in patients with type 2 diabetes," N. Engl. J. Med. (2008) 358:2560-2572.

Pederson, R. A. et al., "Gastric inhibitory polypeptide. Its physiologic release and insulinotropic action in the dog," Diabetes (1975) 24:1050-1056.

Pick, A. et al., "Role of apoptosis in failure of beta-cell mass compensation for insulin resistance and beta-cell defects in the male Zucker diabetic fatty rat," Diabetes (1998) 47:358-364.

Possenti, R. et al., "Expression, processing, and secretion of the neuroendocrine VGF peptides by INS-1 cells," Endocrinology (1999) 140:3727-3735.

Reaven, G. M. et al., "Ranting lecture 1988. Role of insulin resistance in human disease," Diabetes (1988) 37:1595-1607.

Reimer, M. K. et al., "Long-term inhibition of dipeptidyl peptidase IV improves glucose tolerance and preserves islet function in mice," Eur. J. Endocrinol. (2002) 146:717-727.

Ritzel, R. A. et al., "Relationship between beta-cell mass and fasting blood glucose concentration in humans," Diabetes Care (2006) 29:717-718.

Roberge, J. N. et al., "Secretion of proglucagon-derived peptides in response to intestinal luminal nutrients," Endocrinology (1991) 128:3169-3174.

Ronnebaum et al., "A Pyruvate Cycling Pathway Involving Cytosolic NADP-dependent Isocitrate Dehydrogenase Regulates Gulcose-stimulated Insulin Secretion" J. Biol. Chem. (2006) 281:30593-30602.

Salton, S. R. et al., "Structure of the gene encoding VGF, a nervous system-specific mRNA that is rapidly and selectively induced by nerve growth factor in PC12 cells," Mol. Cell. Biol. (1991) 11:2335-2349.

Schebalin, M. et al., "Stimulation of insulin and glucagon secretion by vasoactive intestinal peptide," Am. J. Physiol. (1977) 232:E197-E200.

Schindler, C., "The metabolic syndrome as an endocrine disease: is there an effective pharmacotherapeutic strategy optimally targeting the pathogenesis?," Ther. Adv. Cardiovasc. Dis. (2007) 1:7-26.

Schisler, J.C. et al., "Stimulation of human and rat islet beta-cell proliferation with retention of function by the homeodomain transcription factor Nkx6.1," Mol. Cell Biol. (2008) 28:3465-3476.

Stephens, S.B. et al., "Regulation of islet beta-cell function by the Nkx6.1 transcription program," Duke Department of Pharmacology & Cancer Biology Annual Retreat (Sep. 28, 2007), 1 page.

Stephens, S.B. et al, "Regulation of insulin secretion by VGF-derived peptides," Islet and Beta Cell Biology Keystone Symposium, Snowbird, Utah (Apr. 8 & 9, 2008), 3 pages.

Stephens, S.B., "JDRF File No. 3-2007-560," JDRF Progress Report (Aug. 28, 2008), 7 pages.

Stephens, S.B., "Regulation of islet beta-cell function by VGF-derived peptides," Duke Department of Pharmacology & Cancer Biology Annual Retreat (Sep. 26, 2008), 1 page.

Stephens, S.B. et al., "Regulation of islet beta-cell function by VGF-derived peptides," Keystone Symposium on Type 2 diabetes and insulin resistance (Jan. 23, 2009), 1 page.

Stephens, S.B., "A VGFderived peptide improves glycemic control and insulin sensitivity in diabetic rodents," Grant application submitted to American Heart Association (Feb. 2, 2009), 13 pages.

Stoffers, D. A. et al., "Insulinotropic glucagon-like peptide 1 agonists stimulate expression of homeodomain protein IDX-1 and increase islet size in mouse pancreas," Diabetes (2000) 49:741-748.

Szecowka, J. et al., "The interaction of vasoactive intestinal polypeptide (VIP), glucose and arginine on the secretion of insulin, glucagon and somatostatin in the perfused rat pancreas," Diabetologia (1980) 19:137-142.

Taniguchi, C. M. et al., "Critical nodes in signalling pathways: insights into insulin action," Nat. Rev. Mol. Cell. Biol. (2006) 7:85-96.

Thorens, B. et al., "Expression cloning of the pancreatic beta cell receptor for the gluco-incretin hormone glucagon-like peptide 1," Proc. Natl. Acad. Sci. U.S.A. (1992) 89:8641-8645.

(56) References Cited

OTHER PUBLICATIONS

Trani, E. et al., "Isolation and characterization of VGF peptides in rat brain. Role of PC1/3 and PC2 in the maturation of VGF precursor," J. Neurochem. (2002) 81:565-574.

UK Prospective Diabetes Study (UKPDS) Group, "Effect of intensive blood-glucose control with metformin on complications in overweight patients with type 2 diabetes (UKPDS 34)," Lancet (1998) 352:854-865.

Uk Prospective Diabetes Study (UKPDS) Group, "Intensive blood-glucose control with sulphnoylureas or insulin compared with conventional treatment and risk of complications in patients with type 2 diabetes (UKPDS 33)," Lancet (1998) 352:837-853.

Unger, R. H. et al., "Entero-insular axis," Arch. Intern. Med. (1969) 123:261-266.

Usdin, T. B. et al., "Gastric inhibitory polypeptide receptor, a member of the secretin-vasoactive intestinal peptide receptor family, is widely distributed in peripheral organs and the brain," Endocrinology (1993) 133:2861-2870.

Van Den Pol, A. N. et al., "Hypothalamic expression of a novel gene product. VGF: immunocytochemical analysis," J. Neurosci. (1989) 9:4122-4137.

Watson, E. et al., "VGF ablation blocks the development of hyperinsulinemia and hyperglycemia in several mouse models of obesity," Endocrinology (2005) 146:5151-5163.

Weir, G. C. et al., "Five stages of evolving beta-cell dysfunction during progression to diabetes," Diabetes (2004) 53:S16-S21.

Xu, G. et al., "Exendin-4 stimulates both beta-cell replication and neogenesis, resulting in increased beta-cell mass and improved glucose tolerance in diabetic rats," Diabetes (1999) 48:2270-2276.

Yada, T. et al., "Pituitary adenylate cyclase activating polypeptide is an extraordinarily potent intra-pancreatic regulator of insulin secretion from islet beta-cells," J. Biol. Chem. (1994) 269:1290-1293.

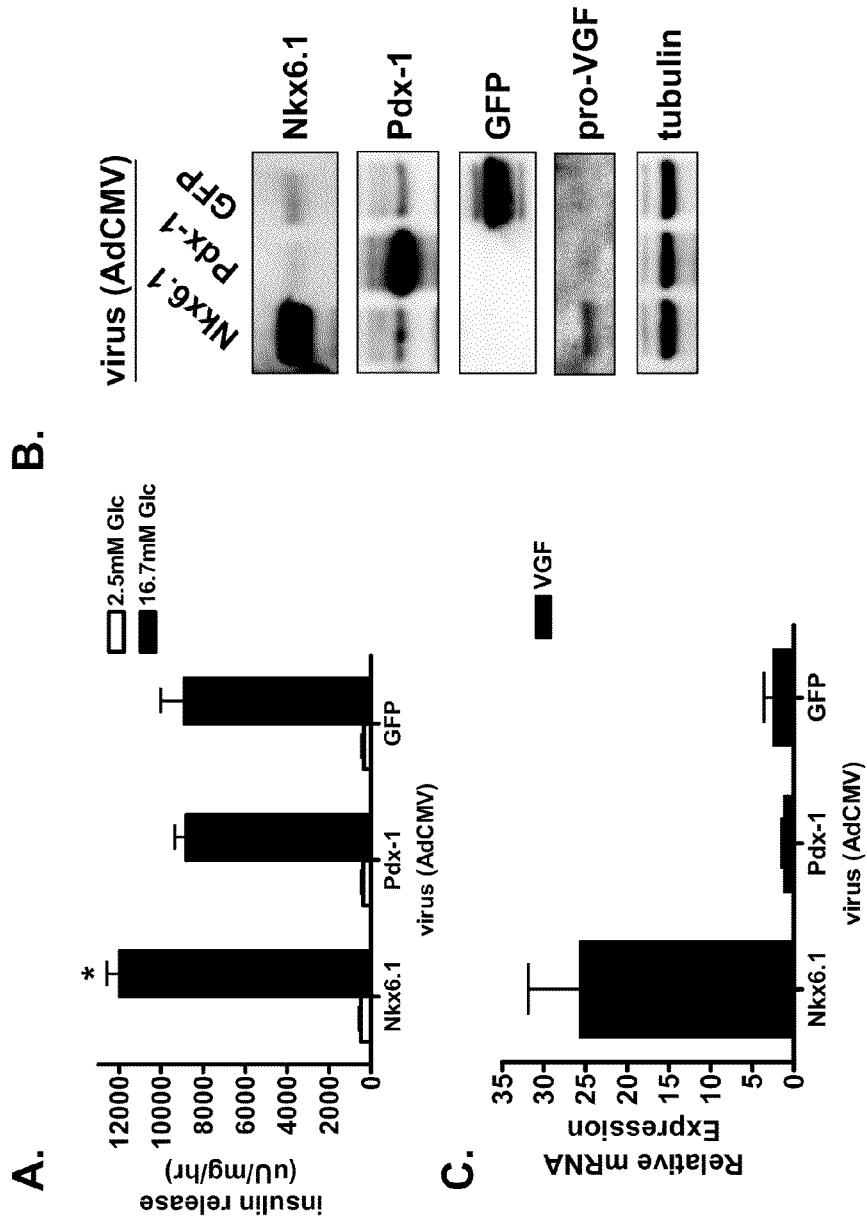
Figure 1. Overexpression of Nkx6.1, but not Pdx-1, enhances GSIS in primary rat islets

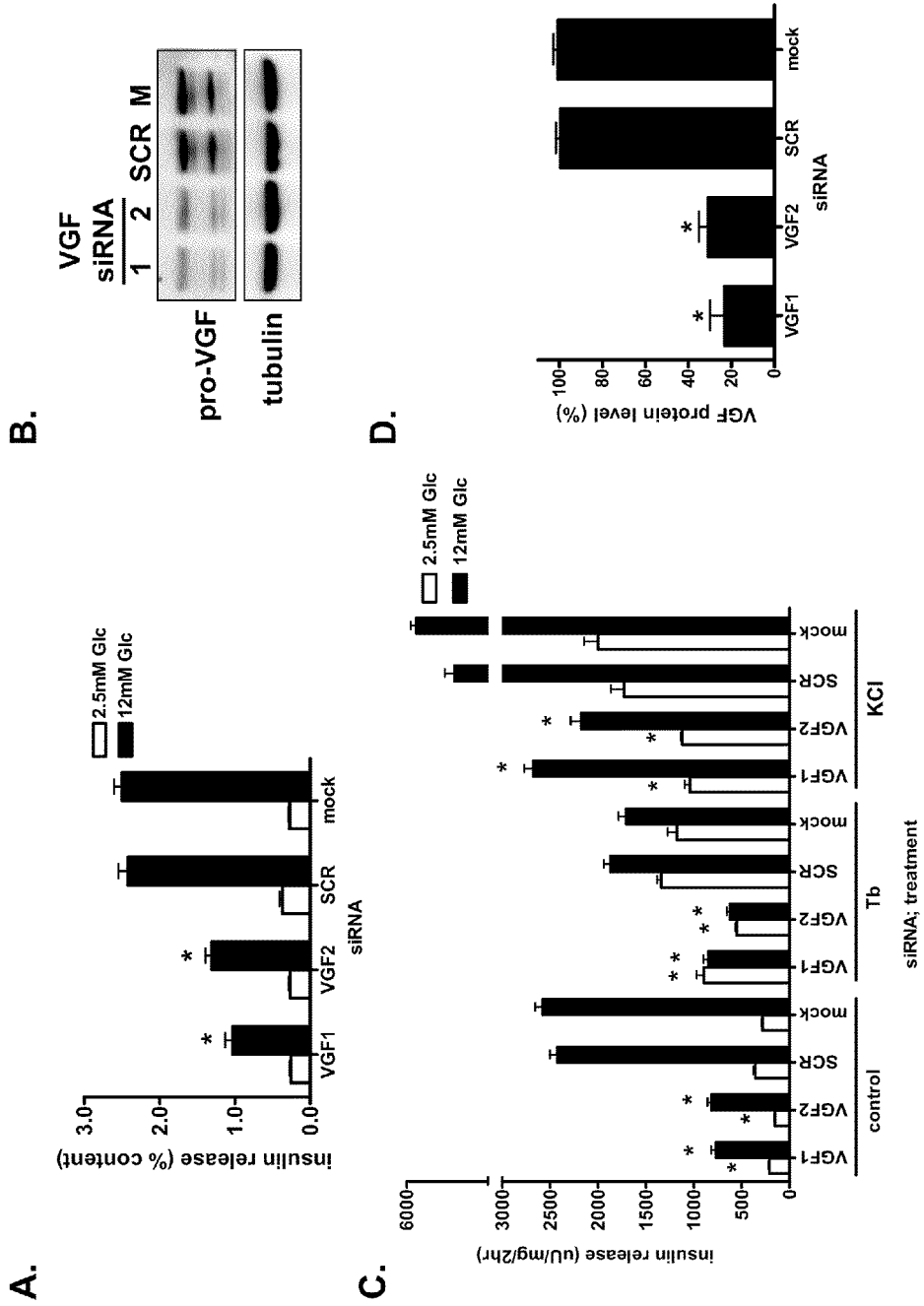
Figure 2. VGF suppression attenuates insulin secretion stimulated by either glucose or direct membrane depolarization

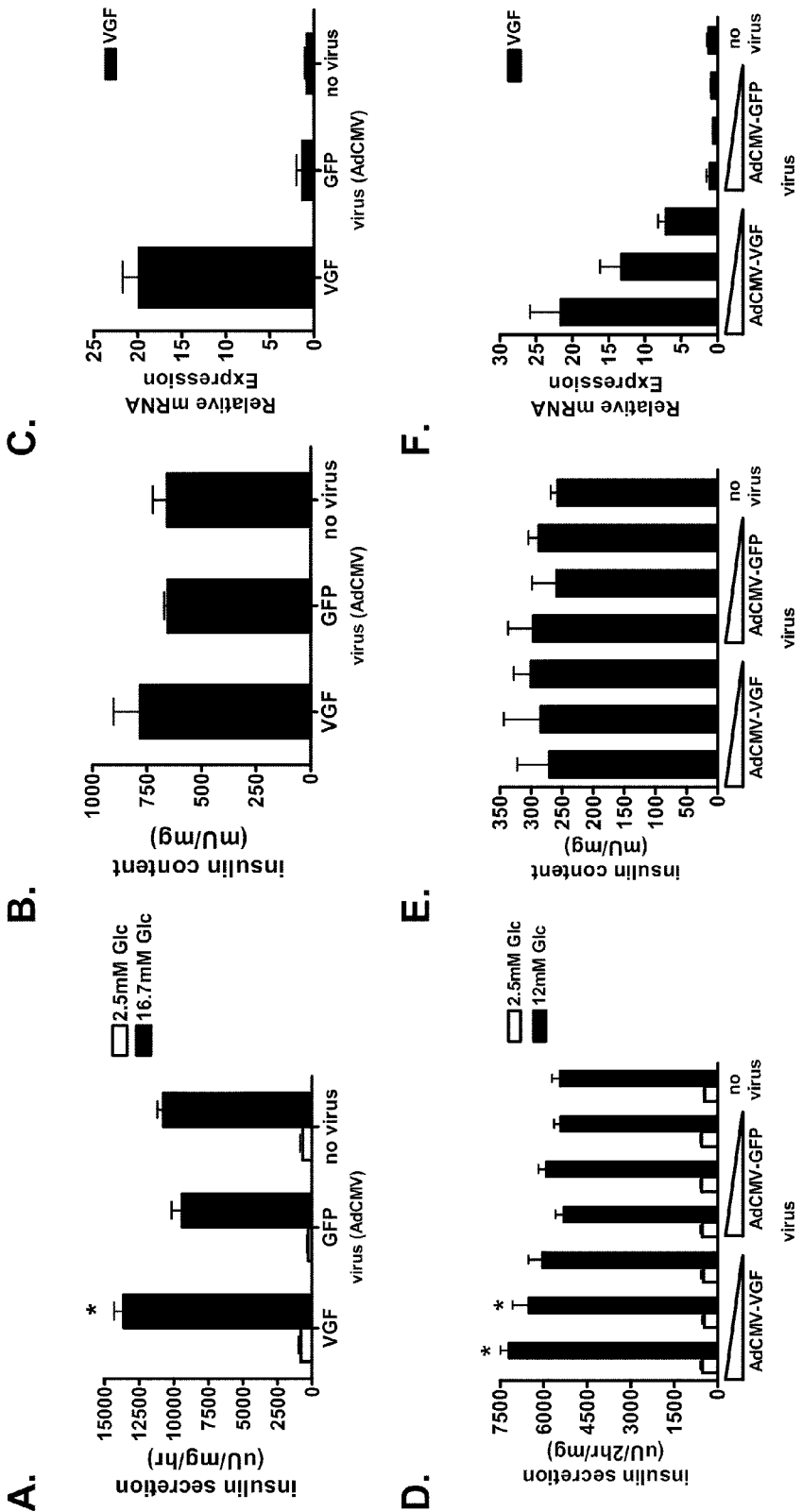
Figure 3. Overexpression of VGF enhances GSIS in primary islets and 832/3 cells

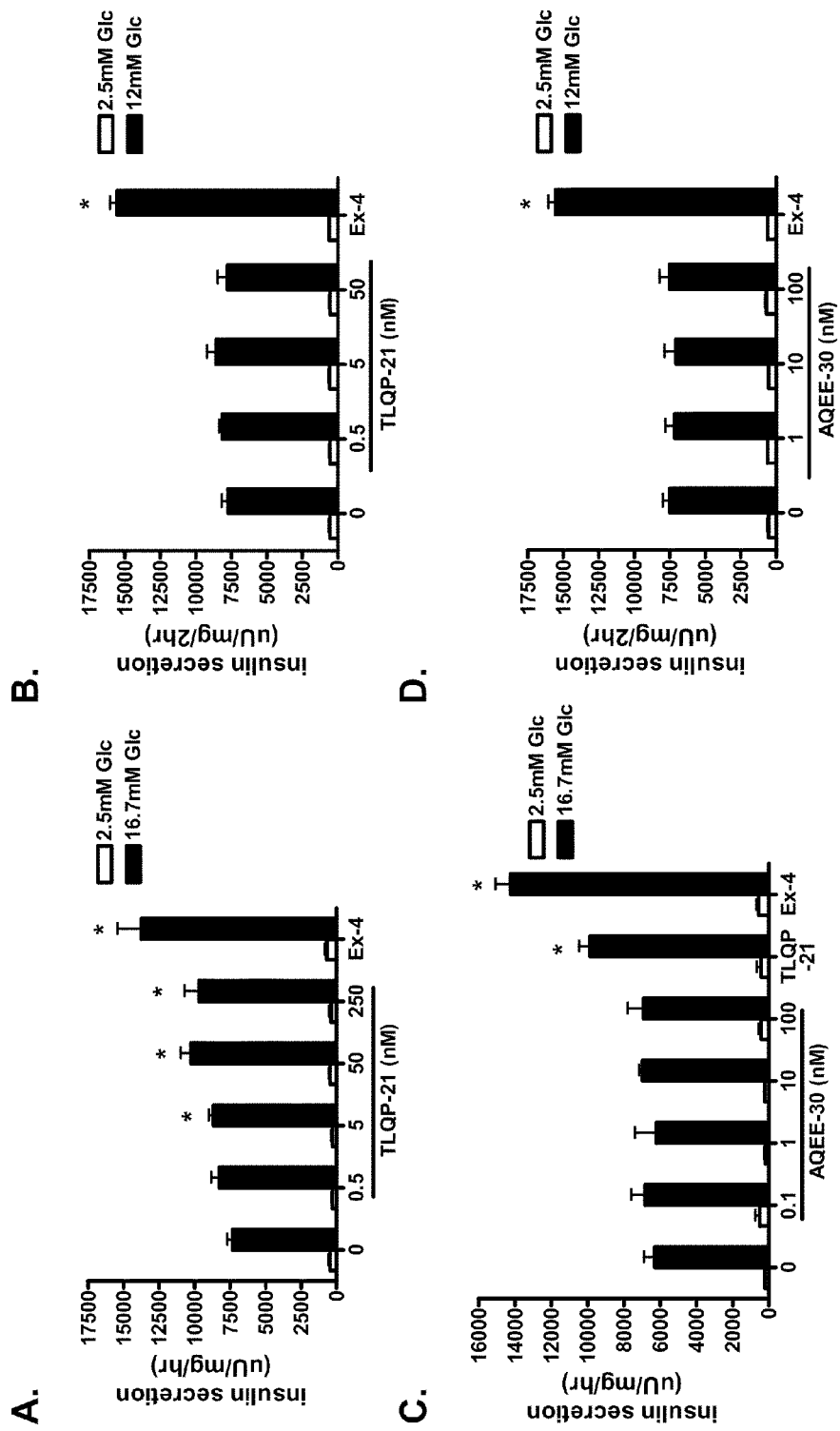
Figure 4. The C-terminal VGF peptide TLQP-21 potentiates GSIS in primary rat islets, but not 832/3 insulinoma cells

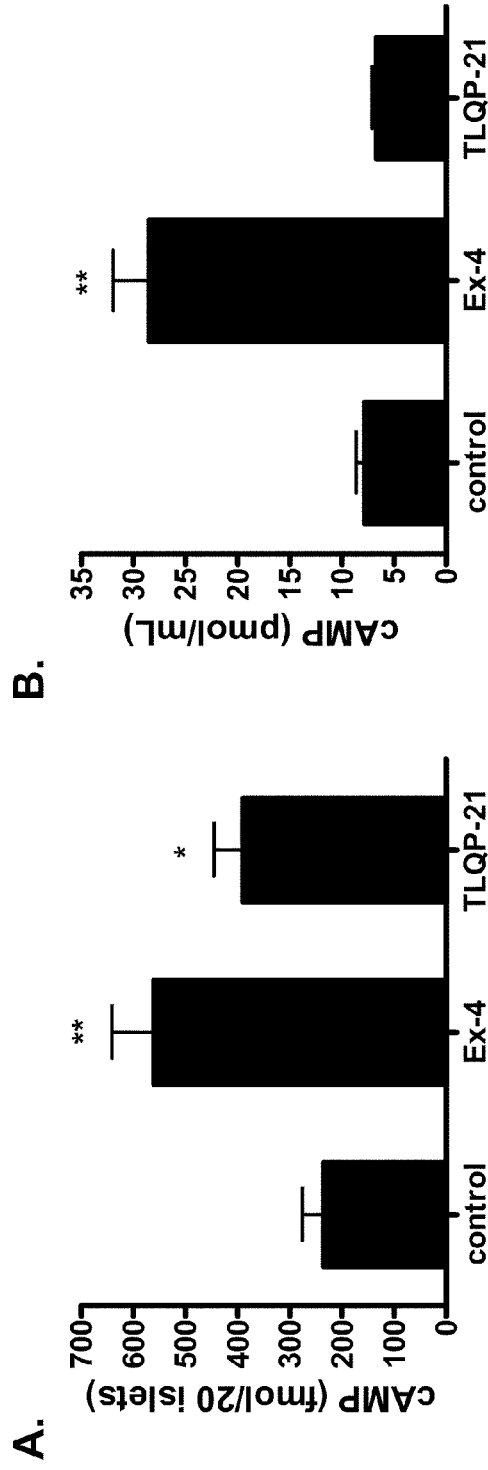
Figure 5. TLQP-21 elevates cAMP levels in primary rat islets, but not 832/3 Insulinoma cells

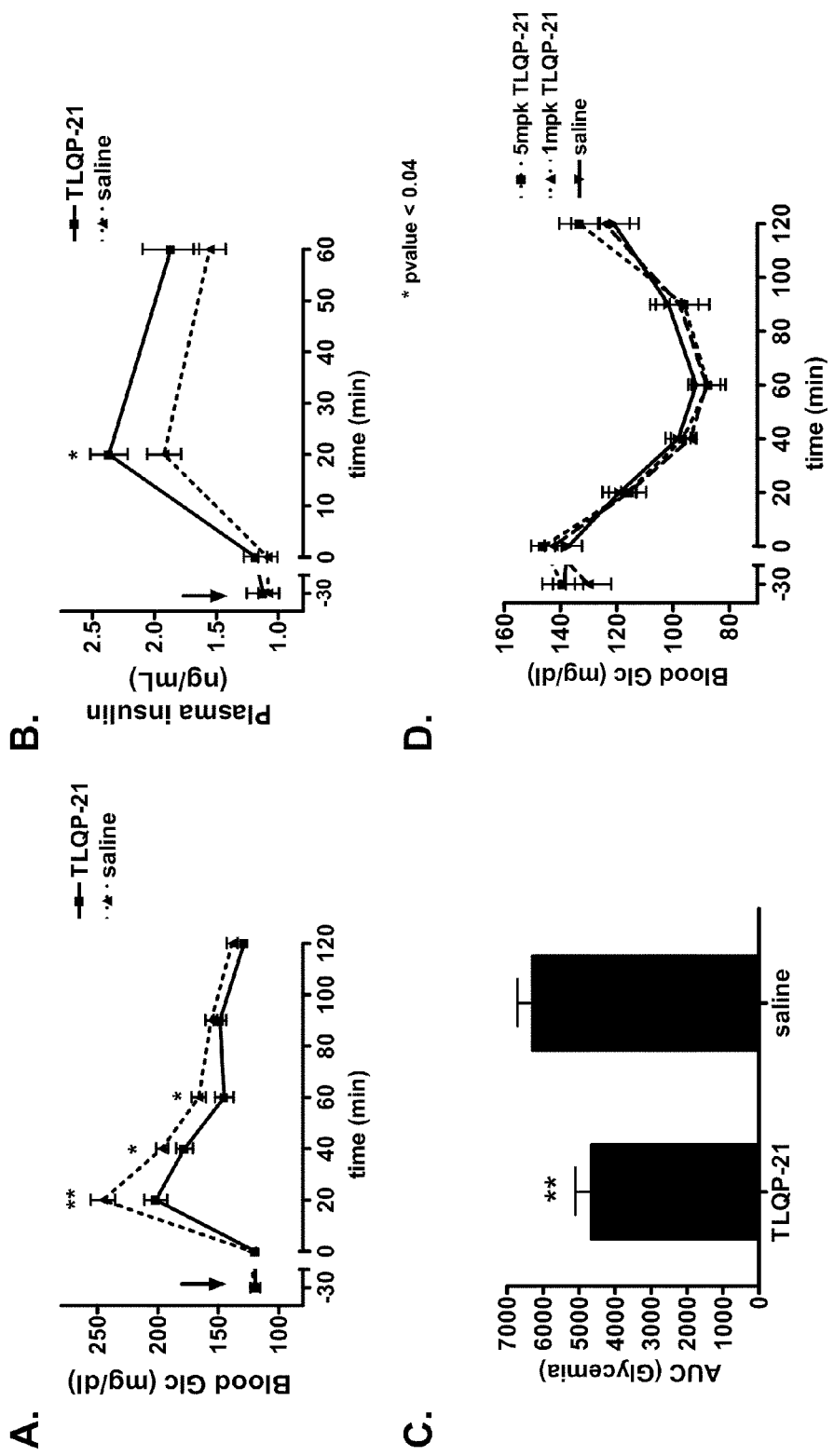

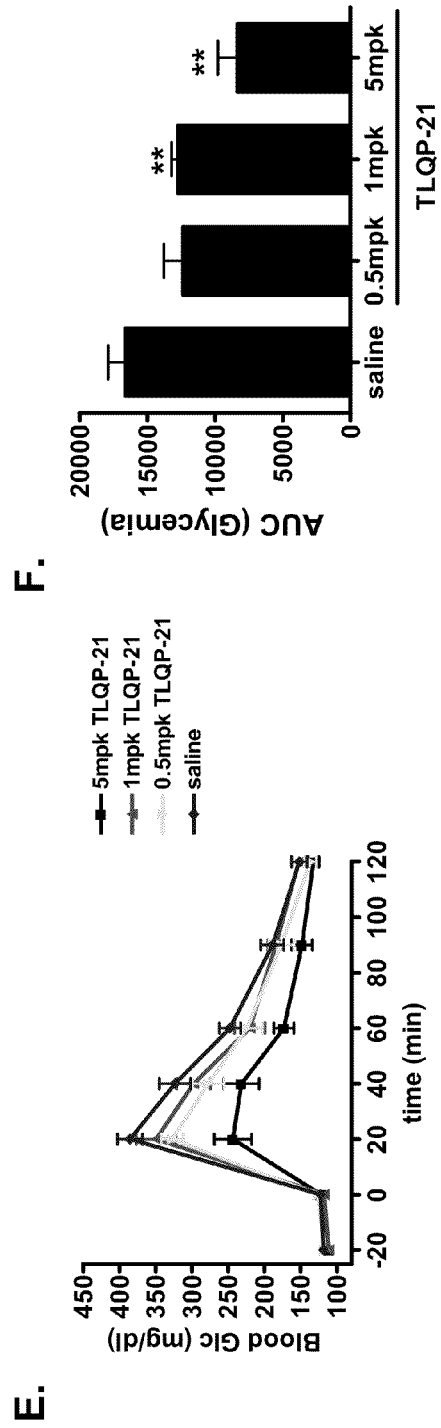
Fig. 6 (cont.) TLQP-21 increases glucose dependent insulin release and reduces glycemic excursion in healthy (Wistar) rats Figure 7. Acute treatment of pre-diabetic ZDF (*fa/fa*) rats improves glucose tolerance
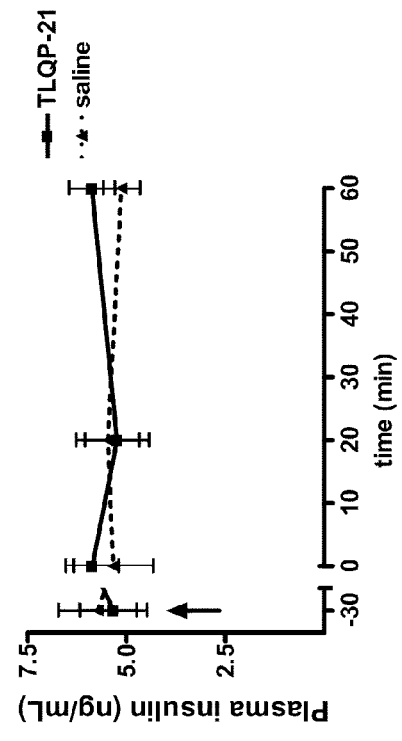
A.
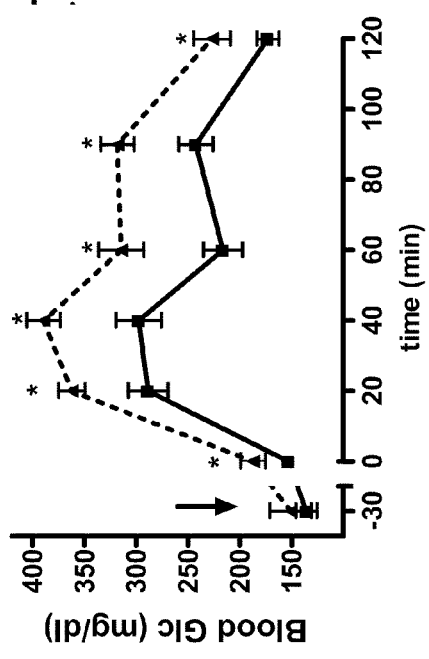
B.

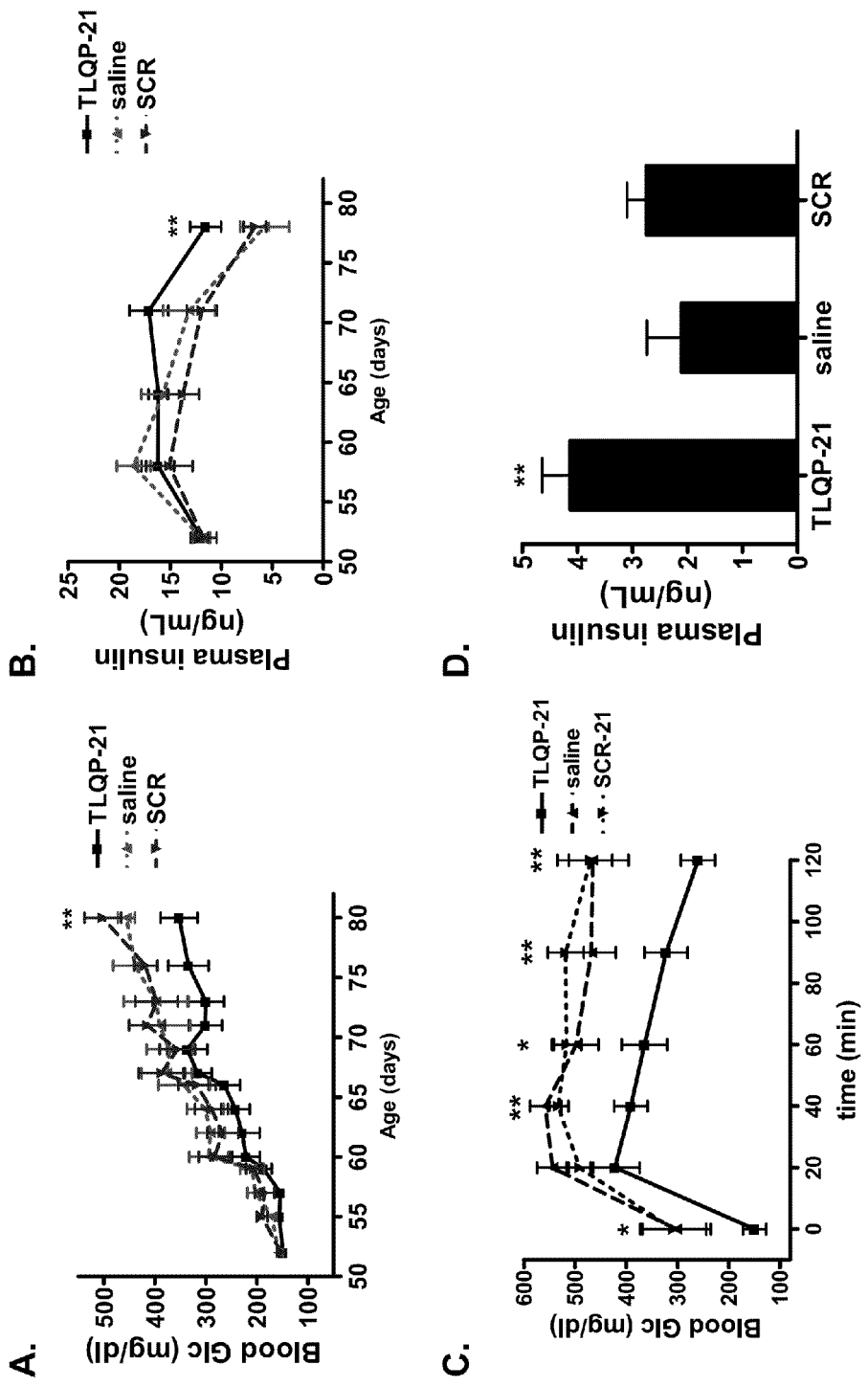

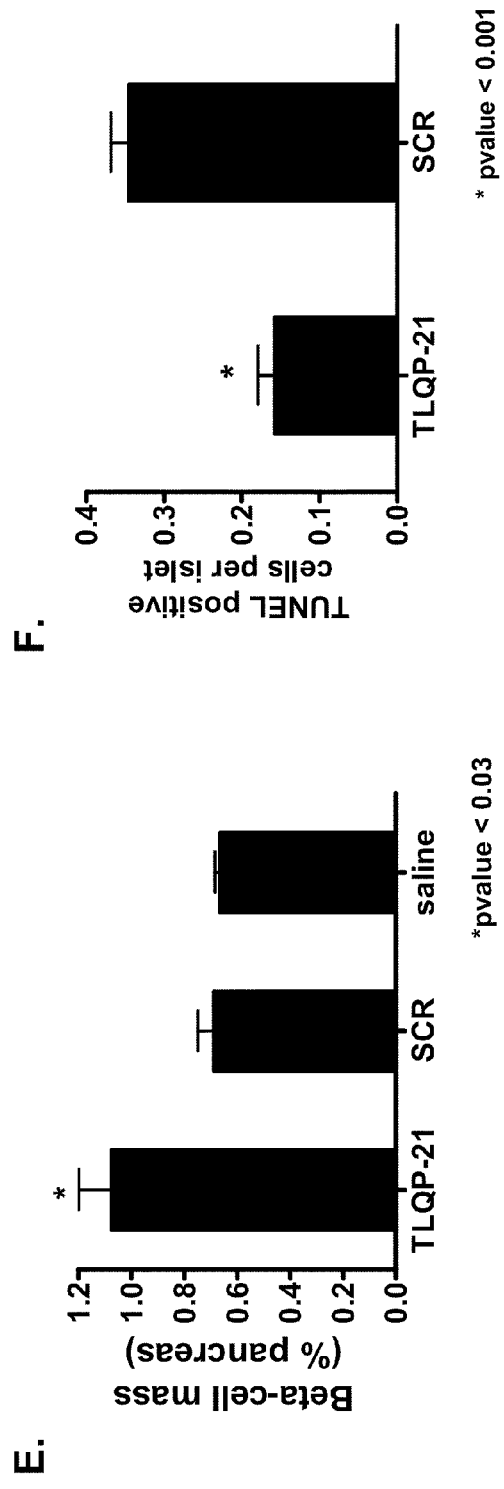
Figure 8 (cont). Treatment (4wk) of ZDF (fa/fa) rats with TLQP-21 delays the onset of overt diabetes

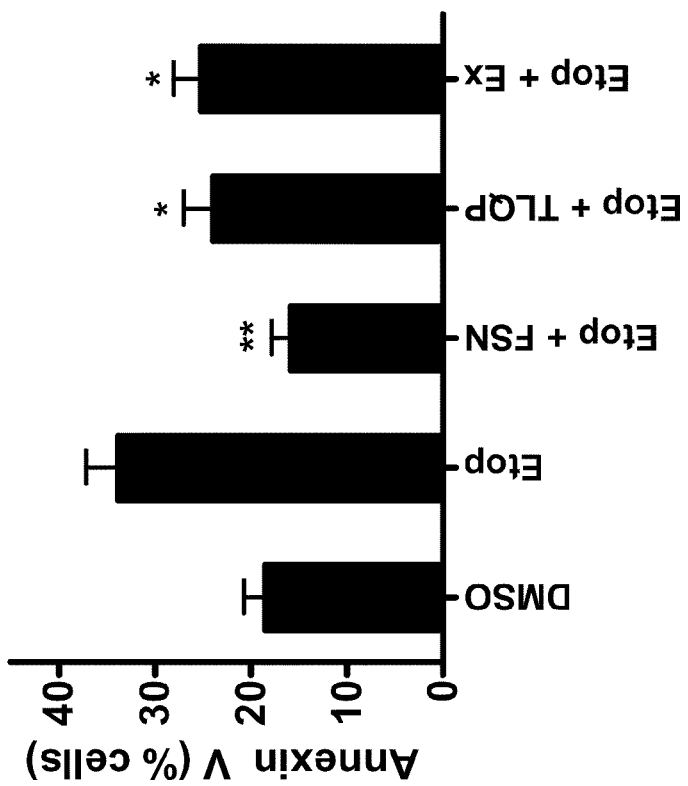
Figure 9. TLQP-21 protects against etoposide-induced apoptosis in isolated rat islets

SEQUENCE LISTING

<160> NUMBER OF SEQ ID NOS: 15

<210> SEQ ID NO 1
<211> LENGTH: 615
<212> TYPE: PRT
<213> ORGANISM: Homo sapiens

<400> SEQUENCE: 1

Met Lys Ala Leu Arg Leu Ser Ala Ser Ala Leu Phe Cys Leu Leu Leu
1               5                   10                  15

Ile Asn Gly Leu Gly Ala Ala Pro Pro Gly Arg Pro Glu Ala Gln Pro
            20                  25                  30

```
Pro Pro Leu Ser Ser Glu His Lys Glu Pro Val Ala Gly Asp Ala Val
        35                  40                  45
Pro Gly Pro Lys Asp Gly Ser Ala Pro Glu Val Arg Gly Ala Arg Asn
    50                  55                  60
Ser Glu Pro Gln Asp Glu Gly Glu Leu Phe Gln Gly Val Asp Pro Arg
65                  70                  75                  80
Ala Leu Ala Ala Val Leu Leu Gln Ala Leu Asp Arg Pro Ala Ser Pro
                85                  90                  95
Pro Ala Pro Ser Gly Ser Gln Gln Gly Pro Glu Glu Ala Ala Glu
                100                 105                 110
Ala Leu Leu Thr Glu Thr Val Arg Ser Gln Thr His Ser Leu Pro Ala
            115                 120                 125
Pro Glu Ser Pro Glu Pro Ala Ala Pro Pro Arg Pro Gln Thr Pro Glu
        130                 135                 140
Asn Gly Pro Glu Ala Ser Asp Pro Ser Glu Glu Leu Glu Ala Leu Ala
145                 150                 155                 160
Ser Leu Leu Gln Glu Leu Arg Asp Phe Ser Pro Ser Ala Lys Arg
                165                 170                 175
Gln Gln Glu Thr Ala Ala Ala Glu Thr Glu Thr Arg Thr His Thr Leu
            180                 185                 190
Thr Arg Val Asn Leu Glu Ser Pro Gly Pro Glu Arg Val Trp Arg Ala
        195                 200                 205
Ser Trp Gly Glu Phe Gln Ala Arg Val Pro Glu Arg Ala Pro Leu Pro
    210                 215                 220
Pro Pro Ala Pro Ser Gln Phe Gln Ala Arg Met Pro Asp Ser Gly Pro
225                 230                 235                 240
Leu Pro Glu Thr His Lys Phe Gly Glu Gly Val Ser Ser Pro Lys Thr
                245                 250                 255
His Leu Gly Glu Ala Leu Ala Pro Leu Ser Lys Ala Tyr Gln Gly Val
            260                 265                 270
Ala Ala Pro Phe Pro Lys Ala Arg Arg Pro Glu Ser Ala Leu Leu Gly
        275                 280                 285
Gly Ser Glu Ala Gly Arg Leu Leu Gln Gln Gly Leu Ala Gln Val
    290                 295                 300
Glu Ala Gly Arg Arg Gln Ala Glu Ala Thr Arg Gln Ala Ala Ala Gln
305                 310                 315                 320
Glu Glu Arg Leu Ala Asp Leu Ala Ser Asp Leu Leu Gln Tyr Leu
                325                 330                 335
Leu Gln Gly Gly Ala Arg Gln Arg Gly Leu Gly Gly Arg Gly Leu Gln
            340                 345                 350
Glu Ala Ala Glu Glu Arg Glu Ser Ala Arg Glu Glu Glu Ala Glu
        355                 360                 365
Gln Glu Arg Arg Gly Gly Glu Glu Arg Val Gly Glu Glu Asp Glu Glu
    370                 375                 380
Ala Ala Glu Ala Glu Ala Gly Ala Glu Glu Ala Arg Ala Arg Gln
385                 390                 395                 400
Asn Ala Leu Leu Phe Ala Glu Glu Glu Asp Gly Glu Ala Gly Ala Glu
                405                 410                 415
Asp Lys Arg Ser Gln Glu Glu Thr Pro Gly His Arg Arg Lys Glu Ala
            420                 425                 430
Glu Gly Thr Glu Glu Gly Gly Glu Glu Asp Asp Glu Glu Met Asp
        435                 440                 445
Pro Gln Thr Ile Asp Ser Leu Ile Glu Leu Ser Thr Lys Leu His Leu
            450                 455                 460
```

Pro Ala Asp Asp Val Val Ser Ile Ile Glu Glu Val Glu Glu Lys Arg
465                 470                 475                 480

Lys Arg Lys Lys Asn Ala Pro Pro Glu Pro Val Pro Pro Pro Arg Ala
            485                 490                 495

Ala Pro Ala Pro Thr His Val Arg Ser Pro Gln Pro Pro Pro Pro Ala
            500                 505                 510

Pro Ala Pro Ala Arg Asp Glu Leu Pro Asp Trp Asn Glu Val Leu Pro
            515                 520                 525

Pro Trp Asp Arg Glu Glu Asp Glu Val Tyr Pro Pro Gly Pro Tyr His
        530                 535                 540

Pro Phe Pro Asn Tyr Ile Arg Pro Arg Thr Leu Gln Pro Pro Ser Ala
545                 550                 555                 560

Leu Arg Arg Arg His Tyr His His Ala Leu Pro Pro Ser Arg His Tyr
                565                 570                 575

Pro Gly Arg Glu Ala Gln Ala Arg Arg Ala Gln Glu Glu Ala Glu Ala
            580                 585                 590

Glu Glu Arg Arg Leu Gln Glu Gln Glu Glu Leu Glu Asn Tyr Ile Glu
            595                 600                 605

His Val Leu Leu Arg Arg Pro
610                 615

<210> SEQ ID NO 2
<211> LENGTH: 2615
<212> TYPE: DNA
<213> ORGANISM: Homo sapiens

<400> SEQUENCE: 2
gcgagctagc cgcccggagc cgcgccgacc cagctgagcc cagcccacgg gacgccagac      60
ctcgaccgtc gctcctaccc cggccaccgc tcggagccga ggcggacgcg tcccgatctt     120
cccctgtccc caccctgccc cgaccctcct ctccacctct cgcgtcgtga caccagctgt     180
ctccggcagc ctcttggtca tgaaagccct cagattgtcg gcttccgccc tcttctgcct     240
tctgctgatc aacgggttag ggcagcaccc cctggtcgc cctgaggcgc agcctcctcc     300
tctcagctct gagcataaag agccggtagc cggggacgca gtgcccgggc aaaggatgg      360 cagcgcccca gaggtccgag cgctcggaa ttccgagccg caggacgagg gagagctttt     420
ccagggcgtg atccccggg cgctggccgc ggtgctgctg caggcactcg accgtcccgc     480 ctcaccccg gcaccaagcg gctcccagca ggggccggag gaagaagcag ctgaagctct     540
gctgaccgag accgtgcgca gccagaccca cagcctcccg gcgccggaga gcccggagcc     600
cgcggctccg cctcgccctc agactccgga gaatgggccc gaggcgagcg atccctccga     660
ggagctcgag gcgctagcgt ccctgctcca ggaactgcga gatttcagtc caagtagcgc     720
caagcgccag caggagacgg cggcagcaga cacggaaacc cgcacgcaca cgctgacccg     780
agtgaatctg gagagcccgg ggccagagcg cgtatggcgc gcttcctggg gagagttcca     840
ggcgcgtgtc ccggagcgcg cgcccctgcc gccccggcc ccctctcaat tccaggcgcg     900
tatgcccgac agcgggcccc ttcccgaaac ccacaagttc ggggaaggag tgtcctcccc     960
caaaacacac ctaggcgagg cattggcacc cctgtccaag gcgtaccaag gcgtggccgc    1020
cccgttcccc aaggcgcgcc ggccggagag cgcactcctg gcggctccg aggcgggcga    1080 gcgccttctc cagcaagggc tggcgcaggt ggaggccggg cggcggcagg cggaggccac    1140
gcggcaggcc gcggcgcagg aagagcggct ggccgacctc gcctcggacc tgctgctcca    1200
gtatttgctg cagggcgggg cccggcagcg cggcctcggg ggtcgggggc tgcaggaggc    1260

```
ggcggaggag cgagagagtg caagggagga ggaggaggcg gagcaggaga gacgcggcgg   1320
ggaggagagg gtgggggaag aggatgagga ggcggccgag gcggaggcag aggcggagga   1380
ggcggagagg gcgcggcaga acgcgctcct gttcgcggag gaggaggacg gggaagccgg   1440
cgccgaggac aagcgctccc aggaggagac gccgggccac cggcggaagg aggccgaggg   1500
gacagaggag ggcggggagg aggaggacga cgaggagatg gatccgcaga cgatcgacag   1560
cctcattgag ctgtccacca aactccacct gccagcggac gacgtggtca gcatcatcga   1620
ggaggtggag gagaagcgga agcggaagaa gaacgcccct cccgagcccg tgccgccccc   1680
ccgtgccgcc cccgccccca cccacgtccg ctccccgcag ccccgccccc cgccccgc    1740 tcccgcacga gacgagctgc cggactggaa cgaggtgctc ccgccctggg atcgggagga   1800
ggacgaggtg tacccgccag ggccgtacca cccttcccc aactacatcc ggccgcggac     1860
actgcagccg ccctcggcct tgcgccgccg ccactaccac cacgccttgc cgccttcgcg   1920
ccactatccc ggccgggagg cccaggcgcg gcgcgcgcag gaggaggcgg aggcggagga   1980
gcgccggctg caggagcagg aggagctgga gaattacatc gagcacgtgc tgctccggcg   2040
cccgtgactg cccttcccgg tcccgccccc gcgcgccccc gccgcgcgcg cgcgccggcg   2100
cccccctccg tgttgcccgc tccccctcgg tgtttgcatg cgccccggcc ctgccccttg   2160
gccctgcccc tgtccccggg ctgcgtcggg acctgccaga ccccctccc gggtcctgag     2220 cccgaactcc cagagctcac ccgcgggtga ccggggccca gcccaggagg gcgggtggtt   2280
tgtgcgagtt cccttgccac gcggggcccc ggccccatca gtccctctg gggacgtccc     2340 cgtcggaaac cggaaaaagc agttccagtt aattgtgtga agtgtgtctg tctccagccc   2400
ttcgggcctc ccacgagccc ctccagcctc tccaagtcgc tgtgaattga ccccttcttt   2460
cctttctctg ttgtaaatac ccctcacgga ggaaatagtt ttgctaagaa ataaaagtga   2520
ctattttatt aggaaaaaaa aaaaaaaaaa aaaaaaaaaa aaaaaaaaaa aaaaaaaaa    2580 aaaaaaaaaa aaaaaaaaaa aaaaaaaaaa aaaaa                               2615
```

<210> SEQ ID NO 3
<211> LENGTH: 617
<212> TYPE: PRT
<213> ORGANISM: Rattus norvegicus

<400> SEQUENCE: 3

```
Met Lys Thr Phe Thr Leu Pro Ala Ser Val Leu Phe Cys Phe Leu Leu
1               5                   10                  15

Leu Ile Arg Gly Leu Gly Ala Ala Pro Pro Gly Arg Ser Asp Val Tyr
            20                  25                  30

Pro Pro Leu Gly Ser Glu His Asn Gly Gln Val Ala Glu Asp Ala
        35                  40                  45

Val Ser Arg Pro Lys Asp Asp Ser Val Pro Glu Val Arg Ala Ala Arg
    50                  55                  60

Asn Ser Glu Pro Gln Asp Gln Gly Glu Leu Phe Gln Gly Val Asp Pro
65                  70                  75                  80

Arg Ala Leu Ala Ala Val Leu Leu Gln Ala Leu Asp Arg Pro Ala Ser
                85                  90                  95

Pro Pro Ala Val Pro Ala Gly Ser Gln Gln Gly Thr Pro Glu Glu Ala
            100                 105                 110

Ala Glu Ala Leu Leu Thr Glu Ser Val Arg Ser Gln Thr His Ser Leu
        115                 120                 125

Pro Ala Ser Glu Ile Gln Ala Ser Ala Val Ala Pro Pro Arg Pro Gln
```

```
              130                 135                 140
Thr Gln Asp Asn Asp Pro Glu Ala Asp Arg Ser Glu Leu Glu
145                 150                 155                 160

Ala Leu Ala Ser Leu Leu Gln Glu Leu Arg Asp Phe Ser Pro Ser Asn
                165                 170                 175

Ala Lys Arg Gln Gln Glu Thr Ala Ala Glu Thr Glu Thr Arg Thr
            180                 185                 190

His Thr Leu Thr Arg Val Asn Leu Glu Ser Pro Gly Pro Glu Arg Val
                195                 200                 205

Trp Arg Ala Ser Trp Gly Glu Phe Gln Ala Arg Val Pro Glu Arg Ala
    210                 215                 220

Pro Leu Pro Pro Ser Val Pro Ser Gln Phe Gln Ala Arg Met Ser Glu
225                 230                 235                 240

Asn Val Pro Leu Pro Glu Thr His Gln Phe Gly Glu Gly Val Ser Ser
                245                 250                 255

Pro Lys Thr His Leu Gly Glu Thr Leu Thr Pro Leu Ser Lys Ala Tyr
                260                 265                 270

Gln Ser Leu Ser Ala Pro Phe Pro Lys Val Arg Arg Leu Glu Gly Ser
        275                 280                 285

Phe Leu Gly Gly Ser Glu Ala Gly Glu Arg Leu Leu Gln Gln Gly Leu
290                 295                 300

Ala Gln Val Glu Ala Gly Arg Arg Gln Ala Ala Thr Arg Gln Ala
305                 310                 315                 320

Ala Ala Gln Glu Glu Arg Leu Ala Asp Leu Ala Ser Asp Leu Leu Leu
                325                 330                 335

Gln Tyr Leu Leu Gln Gly Gly Ala Arg Gln Arg Asp Leu Gly Gly Arg
                340                 345                 350

Gly Leu Gln Glu Thr Gln Glu Arg Glu Asn Glu Arg Glu Glu Glu
        355                 360                 365

Ala Glu Gln Glu Arg Arg Gly Gly Glu Asp Glu Val Gly Glu Glu
        370                 375                 380

Asp Glu Glu Ala Ala Glu Ala Glu Ala Glu Ala Glu Ala Glu Arg
385                 390                 395                 400

Ala Arg Gln Asn Ala Leu Leu Phe Ala Glu Glu Asp Gly Glu Ala
            405                 410                 415

Gly Ala Glu Asp Lys Arg Ser Gln Glu Glu Ala Pro Gly His Arg Arg
                420                 425                 430

Lys Asp Ala Glu Gly Thr Glu Glu Gly Gly Glu Glu Asp Asp Asp
            435                 440                 445

Glu Glu Met Asp Pro Gln Thr Ile Asp Ser Leu Ile Glu Leu Ser Thr
450                 455                 460

Lys Leu His Leu Pro Ala Asp Asp Val Val Ser Ile Ile Glu Glu Val
465                 470                 475                 480

Glu Glu Lys Arg Lys Arg Lys Lys Asn Ala Pro Pro Glu Pro Val Pro
                485                 490                 495

Pro Pro Arg Ala Ala Pro Ala Pro Thr His Val Arg Ser Pro Gln Pro
            500                 505                 510

Pro Pro Pro Ala Pro Ala Arg Asp Glu Leu Pro Asp Trp Asn Glu Val
            515                 520                 525

Leu Pro Pro Trp Asp Arg Glu Glu Asp Glu Val Phe Pro Pro Gly Pro
        530                 535                 540

Tyr His Pro Phe Pro Asn Tyr Ile Arg Pro Arg Thr Leu Gln Pro Pro
545                 550                 555                 560
```

```
Ala Ser Ser Arg Arg Arg His Phe His His Ala Leu Pro Pro Ala Arg
            565                 570                 575

His His Pro Asp Leu Glu Ala Gln Ala Arg Arg Ala Gln Glu Ala
        580                 585                 590

Asp Ala Glu Glu Arg Arg Leu Gln Glu Gln Glu Glu Leu Glu Asn Tyr
        595                 600                 605

Ile Glu His Val Leu Leu His Arg Pro
    610                 615

<210> SEQ ID NO 4
<211> LENGTH: 2636
<212> TYPE: DNA
<213> ORGANISM: Rattus norvegicus

<400> SEQUENCE: 4
cagcgtgctg aagccggagc gagagcgctg ttgctgaccc agctgagccc agctcctagg      60
acgccagccc tcgaccatct ttcatactcc agccacggaa cggagccagg cagacgggt     120
ccggattttc ccctgcccc gaccctcctc tccacctccc gccgtcgtga caccggctgg     180
gggcgacagg aggcactggg tacccagaac gaggattgcg agcgttctct gaccatttgc    240
acgaccccag agattgccac atctttcttg ttctctgcta aacgtttctc ttcggagtct    300
ctggcagccc gttggtcatg aaaaccttca cgttgccagc atccgtcctc ttctgcttcc    360
ttctactcat ccgggggttg ggagcagcac ccccgggcg ctccgatgtt tatcctcctc    420
ccctcggctc tgagcataat gggcaggtag ctgaggacgc agtgtcccgg ccaaaggatg    480
acagcgtccc agaggtccga gcggctcgga attccgagcc tcaggaccag ggagagctct    540
tccagggcgt ggatccccgg cgctggccg cggtactgtt gcaggcactg gaccgtccgg    600
cctcgccccc ggctgtcccg gcaggttccc agcagggaac acccgaagaa gcagcagaag    660
ctctgctgac cgagtccgtg cgcagtcaga cccatagcct cccggcatca gaaatccaag    720
cgtccgctgt ggcgccccct cgccctcaga ctcaggacaa cgatcccgag gcagacgacc    780
gctcagaaga gctggaggca ctagcatcct tgctccaaga acttcgagat tcagtccga    840
gtaatgctaa gcgccagcaa gagacggcgg cagcagagac tgaaacccgc acgcacacgc    900
tgacccgagt caatctggag agccccgggc agagcgcgt atggcgcgct tcctggggag    960
agttccaggc gcgcgtcccg gagcgtgctc ctctgccgcc ctcggtccct tctcaattcc   1020
aggctcgaat gtccgaaaac gttccccttc ccgaaaccca tcagttcggg gaaggagtgt   1080
cctcccctaa aacacatctt ggtgagactt tgacacccct atccaaggcg taccaaagtc   1140
taagtgcccc cttccccaag gtgcgtcggc tcgagggctc attcctgggc ggttccgagg   1200
caggagagcg cctgcttcaa caagggttag ctcaggtaga ggcagggagg aggcaggcgg   1260
aggccacccg gcaggccgca gcgcaagaag agcggctggc cgatctcgcc tccgacctgc   1320
tgctccagta tttgctgcag gcggcgcccc ggcagcgcga tctcggggt cgcgggctgc   1380
aggagacgca gcaagagcgg gagaacgaga gggaggagga ggcggagcag agagacgcg   1440
gtggtgggga ggacgaggtg ggggaagagg atgaggaggc ggcagaggcg gaggcggagg   1500
cagaggaggc ggagagggcg cggcagaacg cgctcctgtt cgccgaggag gaggacgggg   1560
aagccggagc cgaggacaag cgctcccagg aggagcgcc aggccatcgg cggaaggatg   1620
ctgagggac agaggagggc ggggaggagg atgacgacga cgaagagatg gatccgcaga   1680
cgatcgatag tctcattgaa ctgtccacca aactccacct gccagcagac gatgtggtca   1740
gcatcatcga agaggtggag gagaaacgga agcggaagaa gaacgcccct cccgagccgg   1800
```

-continued

```
tgccgccccc cagggctgcc ccagccccga cccatgtccg ctccccgcag ccccacctc    1860 ccgcccggc  ccgggatgag ttgccggact ggaacgaagt actcccaccc tgggatcggg    1920
aggaggatga ggtgtttccc ccggggccct atcacccctt cccaaactac attcggccgc    1980
ggacactgca gccgcccgca tcctcccgcc gccgtcactt ccatcacgcg ttgccacctg    2040
cgcgccacca tcccgatctg gaggcccagg ccaggcgcgc gcaggaggaa gcggacgcgg    2100
aggagcgccg gctgcaggag caggaggagc tggagaatta cattgagcac gtgctgctgc    2160 accgccgtg  acccgcccct gcgcgcccgc tcccaactgc gcgcgccgcc acgcccccc     2220 tccgtgtcgc tcctcctccc tctcggtgtt tgcatgcgcc ccggctccgc ccctcggctg    2280
ccgcccggcc ccgccccaca aggccccgcc ccgggttctg tcaggaccag acctgtcaga    2340
cttctttggg gtctgatcct ggggccagcc caggcgggtg tgtggtttgt gcgagtcccc    2400 ttacacccc  acttcctcca ggggcctcgt ccccatctag tttctctagc gacttcctgg    2460
tcccaaacgg ggaaaagctg ttctatttaa tcgtgtgaag tgtctgtctc ccagccttgg    2520 ggccccgga  gcctcccttc tccaaattgc tgtgaactta cccacatctt gcccttctgt    2580
tgtaaatacc cctcacggag gaaatagttt tgctaagaaa taaaagtgac tatttt        2636
```

<210> SEQ ID NO 5
<211> LENGTH: 5
<212> TYPE: PRT
<213> ORGANISM: Rattus norvegicus

<400> SEQUENCE: 5

Thr Leu Gln Pro Pro
1               5

<210> SEQ ID NO 6
<211> LENGTH: 4
<212> TYPE: PRT
<213> ORGANISM: Rattus norvegicus

<400> SEQUENCE: 6

Arg Arg Arg His
1

<210> SEQ ID NO 7
<211> LENGTH: 6
<212> TYPE: PRT
<213> ORGANISM: Rattus norvegicus

<400> SEQUENCE: 7

His His Ala Leu Pro Pro
1               5

<210> SEQ ID NO 8
<211> LENGTH: 21
<212> TYPE: PRT
<213> ORGANISM: Homo sapiens

<400> SEQUENCE: 8

Thr Leu Gln Pro Pro Ser Ala Leu Arg Arg Arg His Tyr His His Ala
1               5                   10                  15

Leu Pro Pro Ser Arg
            20

<210> SEQ ID NO 9
<211> LENGTH: 21
<212> TYPE: PRT
<213> ORGANISM: Rattus norvegicus

```
<400> SEQUENCE: 9

Thr Leu Gln Pro Pro Ala Ser Ser Arg Arg His Phe His His Ala
1               5                   10                  15

Leu Pro Pro Ala Arg
            20

<210> SEQ ID NO 10
<211> LENGTH: 30
<212> TYPE: PRT
<213> ORGANISM: Homo sapiens

<400> SEQUENCE: 10

Thr Leu Gln Pro Pro Ser Ala Leu Arg Arg His Tyr His His Ala
1               5                   10                  15

Leu Pro Pro Ser Arg His Tyr Pro Gly Arg Glu Ala Gln Ala
            20                  25                  30

<210> SEQ ID NO 11
<211> LENGTH: 30
<212> TYPE: PRT
<213> ORGANISM: Rattus norvegicus

<400> SEQUENCE: 11

Thr Leu Gln Pro Pro Ala Ser Ser Arg Arg His Phe His His Ala
1               5                   10                  15

Leu Pro Pro Ala Arg His His Pro Asp Leu Glu Ala Gln Ala
            20                  25                  30

<210> SEQ ID NO 12
<211> LENGTH: 42
<212> TYPE: PRT
<213> ORGANISM: Homo sapiens

<400> SEQUENCE: 12

Thr Leu Gln Pro Pro Ser Ala Leu Arg Arg His Tyr His His Ala
1               5                   10                  15

Leu Pro Pro Ser Arg His Tyr Pro Gly Arg Glu Ala Gln Ala Arg Arg
            20                  25                  30

Ala Gln Glu Glu Ala Glu Ala Glu Glu Arg
        35                  40

<210> SEQ ID NO 13
<211> LENGTH: 42
<212> TYPE: PRT
<213> ORGANISM: Rattus norvegicus

<400> SEQUENCE: 13

Thr Leu Gln Pro Pro Ala Ser Ser Arg Arg His Phe His His Ala
1               5                   10                  15

Leu Pro Pro Ala Arg His His Pro Asp Leu Glu Ala Gln Ala Arg Arg
            20                  25                  30

Ala Gln Glu Glu Ala Asp Ala Glu Glu Arg
        35                  40

<210> SEQ ID NO 14
<211> LENGTH: 35
<212> TYPE: PRT
<213> ORGANISM: Rattus norvegicus

<400> SEQUENCE: 14

Ala Gln Ala Arg Arg Ala Gln Glu Glu Ala Asp Ala Glu Glu Arg Arg
```

```
                 1               5                  10                 15
Leu Gln Glu Gln Glu Glu Leu Glu Asn Tyr Ile Glu His Val Leu Leu
                        20                  25                 30

His Arg Pro
        35

<210> SEQ ID NO 15
<211> LENGTH: 11
<212> TYPE: PRT
<213> ORGANISM: Rattus norvegicus

<400> SEQUENCE: 15

His His Pro Asp Leu Glu Ala Gln Ala Arg Arg
1               5                  10
```

PEPTIDE THERAPY FOR HYPERGLYCEMIA

CROSS-REFERENCE TO RELATED APPLICATIONS

This application claims priority to U.S. Provisional Application No. 61/167,473, filed Apr. 7, 2009 and U.S. Provisional Application No. 61/167,760, filed Apr. 8, 2009, each of which is incorporated by reference herein in its entirety for any purpose.

STATEMENT REGARDING FEDERALLY SPONSORED RESEARCH

This invention was made with United States government support from National Institute of Health (NIH) and the National Institute of Diabetes and Digestive and Kidney Diseases (NIDDK) grant numbers P01 DK58398 and 2U01-DK-56047-04. The United States government has certain rights in this invention.

INTRODUCTION

The present disclosure is directed to the use of VGF (non-acronymic; unrelated to VEGF) biomolecules and related compositions as mediators to preserve islet β-cell mass and function and to treat hyperglycemia, complications and conditions associated with hyperglycemia and related diseases.

SUMMARY

In some embodiments, methods of treating hyperglycemia are provided in which a patient in need of treatment is administered with a therapeutically effective amount of a VGF biomolecule.

In some embodiments, methods for modulating the blood glucose concentration in a pre-diabetic mammal are provided in which the mammal is administered with a therapeutically effective amount of a VGF biomolecule.

BRIEF DESCRIPTION OF THE FIGURES

FIG. 1: Overexpression of Nkx6.1, but not Pdx-1 enhances GSIS (glucose stimulated insulin secretion) in primary rat islets. Rat islets were treated with recombinant adenoviruses (AdCMV) expressing Nkx6.1, Pdx-1, or GFP and assayed 72 hrs pi. (A) Glucose-stimulated insulin secretion was measured by static incubation in media containing 2.5 mM Glc and 16.7 mM Glc for 1 hr each. (B) Immunoblot analysis of whole cell lysates. (C) Quantitative RT-PCR was used to determine the VGF mRNA expression level. (A-C) Data represent the mean±S.E.M (n=3). * pvalue≤0.01

FIG. 2: Suppression of VGF in 832/3 cells reduces GSIS. 832/13 cells were transfected with siRNA duplexes targeting the VGF mRNA, a non-targeting duplex control (SCR) or mock transfected (A) Cells were assayed for insulin secretion by static incubation in media containing 2.5 mM Glc and then 12 mMGlc for 2 hrs each. (B) Immunoblot analysis of pro-VGF expression from whole cell lysates. (C) Cells were assayed for insulin secretion by static incubation in media containing 2.5 mM Glc and then 12 mMGlc for 2 hrs each. 35 mM KCl or tolbutamide was included as indicated in the secretion buffer. (D) Quantitation of immunoblot analysis of VGF expression. Data represent the mean±S.E.M. (n=3). * pvalue≤0.01

FIG. 3: Overexpression of VGF enhances GSIS in primary islets and 832/3 cells. Rat islets (A-C) or 832/3 cells (D-F) were treated with recombinant adenovirus expressing VGF or GFP and assayed 72 hrs pi. (A) Primary rat islets were assayed for insulin secretion by static incubation in media containing 2.5 mM Glc and then 16.7 mM Glc for 1 hr each. (B, E) Insulin content was determined from whole cell lysates. (C, F) Quantitative RT-PCR was used to determine the level of VGF mRNA expression. (D) 832/3 cells were assayed for insulin secretion by static incubation in media containing 2.5 mM Glc and then 12 mM Glc for 2 hr each. (A-F) Data represent the mean±S.E.M (n=3). * pvalue≤0.01

FIG. 4: The C-terminal VGF peptide TLQP-21 potentiates GSIS in primary rat islets. (A, C) Primary rat islets were assayed for insulin secretion by static incubation in media containing 2.5 mM Glc and then 16.7 mM Glc for 1 hr each. (B, D) 832/3 cells were assayed for insulin secretion by static incubation in media containing 2.5 mM Glc and then 12 mM Glc for 2 hr each. The indicated concentrations of the VGF peptide, TLQP-21, AQEE-30, or exendin-4 (20 nM) were added during both the basal and stimulatory glucose incubations. (C) 50 nM TLQP-21 was used as a positive control. (A-D) Data represent the mean±S.E.M (n=3). * pvalue≤0.01, ** pvalue≤0.002

FIG. 5: TLQP-21 elevates cAMP levels in primary rat islets. (A) Rat islets were assayed for cAMP levels following a 30 min incubation in media containing 16.7 mM Glc with exendin-4 (20 nM) or TLQP-21 (50 nM) relative to the untreated control. (B) 832/3 cells were assayed for cAMP levels following a 30 min incubation in media containing 12 mM Glc with exendin-4 (20 nM) or TLQP-21 (50 nM) relative to the untreated control. Data represent the mean±S.E.M (n=3). * pvalue≤0.01, ** pvalue≤0.002

FIG. 6: TLQP-21 enhances plasma insulin release and reduces glycemic excursion in male Wistar rats. (A-C) Overnight (12 hr) fasted rats were injected (i.p.) with either vehicle (saline) control or 4.5 mg/kg TLQP-21 at 30 min prior to a 1 g/kg glucose bolus (i.p.). (A) Blood glucose was monitored at the indicated times. (B) Blood was sampled from the saphenous vein at the indicated times and assayed for insulin levels. (C) Average area under the curve (AUC) analysis for the glucose tolerance test results. (D) Ad libitum fed rats were injected i.p. with either vehicle (saline) control or 4.5 mg/kg TLQP-21 at 30 min prior to a 1 U/kg insulin challenge. Blood glucose was measured at the indicated times. (E-F) Overnight (12 hr) fasted rats were injected (i.p.) with 5 mg/kg, 1 mg/kg, 0.5 mg/kg TLQP-21, or vehicle saline a 30 min prior to a 2 g/kg glucose bolus. (E) Blood glucose was monitored at the indicated times and (F) average area under the curve (AUC) for the glucose tolerance test results determined. Data represent the mean±S.E.M (A-C, n=12; D, n=5; E-F, n=7). * pvalue≤0.05, ** pvalue≤0.01

FIG. 7: Acute treatment of pre-diabetic ZDF (fa/fa) rats improves glucose tolerance. 10 week old Zucker Diabetic Fatty (fa/fa) rats were fasted overnight (12 hrs) and injected (i.p.) with either 4.5 mg/kg TLQP-21 dissolved in saline or saline alone 30 minutes prior to a 1 g/kg glucose bolus (i.p.). (A) Blood glucose was monitored via percutaneous incision of the tail at the indicated times. (B, C) Blood was sampled from the saphenous vein at the indicated times and assayed for insulin levels. Data are presented as the mean±S.E.M (n=6). * pvalue≤0.01.

FIG. 8: Chronic treatment of ZDF rats with TLQP-21 improves glucose homeostasis and preserves islet β-cell mass. Male Zucker Diabetic Fatty (fa/fa) rats were injected (i.p.) with 5 mg/kg TLQP-21, a scrambled peptide of identical amino acid composition (SCR), or vehicle saline on alternating days for 4 wks beginning at ~7 wks of age (n=8). (A) Ad libitum blood glucose was measured as indicated. (B) Plasma insulin was determined from blood sampled at the indicated time points. (C) Overnight (12 hr) fasted rats were given a 1 g/kg glucose challenge (i.p.) and blood glucose monitored at the indicated times. (D) Plasma insulin levels were assayed from overnight (12 hr) fasted rats. (E) Quantitation of β-cell mass was calculated as the percentage of insulin staining area relative to the total area of pancreas section from 4 independent sections per animal (n≥4 per group) as described in the Materials and Methods section. (F) Quantification of the average number of TUNEL positive, insulin staining cells per islet as described in the Material and Methods section. Data are presented as the mean±S.E.M. * pvalue≤0.05, ** pvalue≤0.01

FIG. 9: TLQP-21 is partially protective against apoptosis in isolated rat islets. Rat islets were treated for 72 hrs with (0.2 mM) etoposide in the presence or absence of TLQP-21 (50 nM), exendin-4 (20 nM), or forskolin (504). Dissociated islet cells were assayed for FITC-conjugated Annexin V staining via flow cytometry. Data are presented as the mean±S.E.M. * pvalue≤0.01, ** pvalue≤0.002.

DETAILED DESCRIPTION

The present disclosure describes the pharmacological uses of VGF polypeptides and related compositions in the treatments of disorders characterized by hyperglycemia, including Diabetes mellitus.

Diabetes mellitus, commonly referred to as diabetes, is the one of the leading causes of death in the United States. It is a chronic disease with associated complications that may include amputations of lower body parts, heart disease, kidney failure, poor wound healing and blindness. Diabetes is categorized into several types, the most common of which are Type I diabetes, Type II diabetes and gestational diabetes, with Type II diabetes accounting for over 90% of all diabetes in the United States.

Type II diabetes, also named non-insulin-dependent diabetes mellitus (NIDDM), is defined by hyperglycemia, caused by peripheral insulin resistance and a deficiency in glucose-controlled insulin release from pancreatic islet beta-cells. Accordingly, NIDDM is characterized by high blood glucose in the context of insulin resistance and relative insulin deficiency. In NIDDM there appears to be a reduction in the pancreatic β-cell mass, several distinct defects in insulin secretion or a decrease in tissue sensitivity to insulin. The symptoms of this form of diabetes include fatigue, frequent urination, thirst, blurred vision, frequent infections and slow healing of sores, diabetic nerve damage and renal disease.

Resistance to the metabolic actions of insulin is characteristic of NIDDM. Insulin resistance is characterized by impaired uptake and utilization of glucose in insulin-sensitive target organs, for example, adipocytes and skeletal muscle, and by impaired inhibition of hepatic glucose output. The functional insulin deficiency and the failure of insulin to suppress hepatic glucose output results in fasting hyperglycemia. Pancreatic β-cells compensate for the insulin resistance by secreting increased levels of insulin. However, the β-cells are unable to maintain this high output of insulin, and, eventually, the glucose-induced insulin secretion falls, leading to the deterioration of glucose homeostasis and to the subsequent development of overt diabetes. Hyperinsulinemia is also linked to insulin resistance, hypertriglyceridaemia and increased plasma concentration of low density lipoproteins. The association of insulin resistance and hyperinsulinemia with these metabolic disorders has been termed has been strongly linked to an increased risk of hypertension and coronary artery disease.

Management of NIDDM and related disorders is often initially through increasing exercise and dietary modification. However, as the condition progresses, medications are typically needed. Current medications for insulin resistance include metformin and agonists of peroxisome proliferator-activated receptor gamma such as thiazolidinediones (TZDs). Metformin is used in the treatment of diabetes in humans (See, e.g., U.S. Pat. No. 3,174,901). Metformin acts primarily to decrease liver glucose production. Troglitazone® is known to work primarily on enhancing the ability of skeletal muscle to respond to insulin and take up glucose. Combination therapy comprising metformin and troglitazone can be used in the treatment of abnormalities associated with diabetes. However, TZD-based treatments may have adverse side effects including fluid retention, congestive heart failure and fatty liver.

Methods of controlling or treating hyperglycemia, complications or conditions associated with hyperglycemia and related diseases or conditions by administering a therapeutically effective amount of a VGF biomolecule (e.g., a VGF polypeptide or polynucleotide encoding the VGF polypeptide) are provided. In some embodiments, methods of modulating blood glucose concentration in a patient having an elevated blood glucose level are provided. VGF, also named VGF nerve growth factor inducible, shares similarities with the polypeptides of the secretogranin/chromogranin family and is an energy homeostasis regulator. VGF is found in the secretory granules of subsets of neurons and endocrine cells. VGF is widely expressed in neuroendocrine cells of the brain, particularly the hypothalamus and hippocampus, enteroendocrine cells of the gut, and pancreatic islet cells. VGF is expressed as a large 67-kDa prohormone and is processed by the subtilisin-like hormone processing enzymes PC 1/3 and/or PC2 to yield a number of distinct peptides. In islet cells, these peptides are stored in large dense core granules and secreted through the regulated secretory pathway in response to secretagogues such as glucose.

A VGF biomolecule may comprise at least part of a VGF polypeptide, or a polynucleotide encoding at least part of a VGF polypeptide. The VGF biomolecule generally has the capacity to modulate blood glucose concentration. The VGF biomolecule may comprise a functional fragment of a VGF polypeptide, or may comprise a polynucleotide encoding a functional fragment of a VGF polypeptide, or a complementary polynucleotide thereof. A VGF biomolecule may include one or more of a polypeptide, peptide, polynucleotide, prohormone, prodrug, fragment, derivative, and/or metabolite.

A VGF polypeptide is a polypeptide sequence comprising at least nine amino acids that have at least about 50% identity with a contiguous sequence of amino acids from an entire VGF polypeptide, such as SEQ ID NO: 1 or SEQ ID NO:3, or a functional fragment thereof. The VGF polypeptide generally has the capacity to modulate blood glucose concentration.

A functional fragment of a VGF polypeptide is a polypeptide that shares identity with the VGF polypeptide but has one or more amino acid differences from the VGF polypeptide. A functional fragment of a VGF polypeptide retains at least some, if not all, of its capacity to modulate blood glucose concentration.

In some embodiments, the VGF polypeptide comprises the following sequence:

Peptide1-X-Peptide2-Z-Peptide3-J-Arg wherein Peptide1 comprises SEQ ID NO. 5 or a sequence having at least about 80% identity with SEQ ID NO. 5 (TLQPP), Peptide2 comprises SEQ ID NO. 6 or a sequence having at least about 75% identity with SEQ ID NO. 6

(RRRH) and Peptide3 comprises SEQ ID NO. 7, or a sequence having at least about 80% identity with SEQ ID NO. 7 (HHALPP). In some embodiments X may be from zero, one, two three four, five, six, seven, eight, nine or ten amino acids, Z may be from zero, one, two, three, four, five, six, seven, eight, nine, or ten amino acids and J may be from zero, one, two, three, four, five, six, seven, eight, nine, or ten amino acids. For example, X may comprise or consist of $X_{aa1}X_{aa2}X_{aa3}$ with $X_{aa1}$ being serine or alanine, $X_{aa2}$ being serine or alanine, and $X_{aa3}$ being serine or leucine, Z may comprise or consist of phenylalanine or tyrosine and J may comprise or consist of serine or alanine.

In some embodiments, the VGF polypeptide is a TLQP-21 polypeptide. A TLQP-21 polypeptide is an amino acid sequence that corresponds to SEQ ID NO:8 (the 21-amino acid sequence from positions 554-574 of SEQ ID NO: 1; human VGF), such as SEQ ID NO:9 (the 21-amino acid sequence from positions 556-576 of SEQ ID NO:3; rat VGF) and has the capacity to modulate blood glucose concentration. A TLQP-21 polypeptide may include additional sequences that do not affect its function, as well as one or more conservative amino acid substitutions, amino acid deletions or a combination thereof, while still retaining the ability to modulate blood glucose concentration.

A comparison of TLQP-21 polypeptides from VGF polypeptides from various mammalian species (rat, mouse, monkey, human, horse, cow) show the following similarities and differences. Residues shown underlined below are 100% conserved between the species. The residues marked as B, J, or O are found with one of two possible amino acids and may represent potential sites for conservative substitutions which would not affect or which may improve binding and/or activity.

<u>TLQPPBBORRRHJHHALPPBR</u>

B=serine or alanine (i.e. small uncharged)
J=phenylalanine or tyrosine (bulky, hydrophobic, aromatic ring)
O=serine or leucine The isolated VGF polypeptides include amino acid sequences that are at least about 25%, 30%, 35%, 40%, 45%, 50%, 55%, 60%, 65%, 70%, 75%, 80%, 85%, 90%, 95%, 96%, 97%, 98% or 99% identical to one or more of polypeptides disclosed herein, including a sequence selected from SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. The polypeptide sequences may be, for example, at least about 5, 7, 8, 9, 10, 11, 12, 13, 14, 15, 16, 17, 18, 19, 20, 21, 22, 23, 24, 25, 26, 26, 28, 29, 30, 31, 32, 33, 34, 35, 36, 37, 38, 39, 40, 41, 42, 43, 44, 45, 46, 47, 48, 49 or 50 amino acids in length, and less than about 200, 195, 190, 185, 180, 175, 170, 165, 160, 155, 150, 145, 140, 135, 130, 125, 120, 115, 110, 105, 100, 95, 90, 85, 80, 75, 70, 65, 60 or 55 amino acids in length.

In some embodiments, the VGF polypeptide comprises a sequence that is least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% identity with SEQ ID NO. 8 or SEQ ID NO: 9, and comprises a first sequence having at least about 40%, at least about 60%, or at least about 80% identity with SEQ ID NO. 5 (TLPPQ), a second sequence having at least about 50% or at least about 75% identity with SEQ ID NO. 6 (RRRH) and a third sequence having at least about 40%, at least about 60%, or at least about 80% identity with SEQ ID NO. 7 (HHALPP).

Percent identity or % identity of a polypeptide is determined by comparing the two sequences using a computer implemented algorithm, specifically, the algorithm of Karlin and Altschul (Proc. Natl. Acad. Sci. 87: 2264-68 (1990), modified Proc. Natl. Acad. Sci. 90: 5873-77 (1993)), using the default parameters.

Polypeptides that are substantially identical share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Conservative amino acids substitution groups include: valine-leucine-isoleucine, phenylalanine-tyrosine, lysine-arginine, alanine-valine, aspartic acid-glutamic acid, and asparagines-glutamine.

Accordingly, polypeptides or proteins that may be used include amino acid sequences that have substantial identity to VGF polypeptides described herein. The polypeptides may include one or more of the amino acid sequences TLQPP (SEQ ID NO:5), RRRH (SEQ ID NO:6) and HHALPP (SEQ ID NO:7).

Examples of VGF polypeptides include, but are not limited to, polypeptides comprising an amino acid sequence selected from SEQ ID NOs: 1, 3, and 5-15, but having one or more conservative amino acid substitutions. Polynucleotides encoding VGF polypeptides, for example, those described here, may also be used in the methods described herein.

Polynucleotide includes reference to a deoxyribonucleotide or ribonucleotide polymer in either single- or double-stranded form. The use of the terms polynucleotide constructs or nucleotide constructs herein is not intended to limit the present invention to nucleotide constructs comprising DNA. Polynucleotide constructs and oligonucleotides composed of ribonucleotides and combinations of ribonucleotides and deoxyribonucleotides, may also be employed in the methods disclosed herein. The nucleotide constructs, nucleic acids, and nucleotide sequences disclosed herein additionally encompass all complementary forms of such constructs, molecules, and sequences.

Examples of VGF polynucleotides include, but are not limited to, polynucleotides that encode a polypeptide comprising an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% identity to at least one amino acid sequence selected from SEQ ID NOs: 1, 3, and 5-15.

In some embodiments, a polynucleotide comprises a contiguous coding sequence encoding a polypeptide comprising an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% identity to at least one amino acid sequence selected from SEQ ID NOs: 1, 3, and 5-15. Contiguous means that the nucleotides of the coding sequence are connected in an unbroken sequence (for example, the coding region of the polynucleotide lacks introns).

Similarity or identity between the polynucleotide sequences may be as defined and determined by the TBLASTN program, of Altschul et al. (1990) *J. Mol. Biol.* 215: 403-10, which is in standard use in the art, or, and this may be preferred, the standard program BestFit, which is part of the Wisconsin Package, Version 8, September 1994 (Genetics Computer Group, 575 Science Drive, Madison, Wis., USA, Wisconsin 53711).

In some embodiments, nucleic acids that selectively hybridize to the exemplified sequences, including hybridizing to the exact complements of these sequences may be used. The specificity of single-stranded DNA to hybridize complementary fragments is determined by the stringency of the reaction conditions. Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

The polynucleotides of the invention may be provided in vectors or other constructs that facilitate delivery of the polynucleotide to the target cells or tissue of the patient. The vector or construct may include a promoter that directs expression of the polynucleotide. An appropriate promoter and other necessary vector sequences are selected so as to be functional in the host, and may include, when appropriate, those naturally associated with the VGF coding sequence. Promoters useful in the practice of the present invention include, but are not limited to, constitutive, inducible, temporally-regulated, developmentally regulated, chemically regulated, tissue-preferred and tissue-specific promoters. The promoter may direct sufficient expression in the patient, cell or tissue to produce a desired effect. Suitable promoters include, without limitation, non-native mammalian promoters such as the early and late promoters from SV40 or promoters derived from murine Moloney leukemia virus, mouse tumor virus, avian sarcoma viruses, adenovirus II, bovine papilloma virus or polyoma, rat insulin promoter, human insulin promoter, pdx-1 promoter, nkx6.1 promoter, and the VGF promoter. In addition, the construct may be joined to an amplifiable gene so that multiple copies of the polynucleotides may be made. The polynucleotide may be expressed to produce a therapeutically effective amount of a VGF polypeptide in a patient, cell or tissue.

In some embodiments, expression and cloning vectors contain a selectable marker polynucleotide, a sequence encoding a protein necessary for survival or growth of a host cell transformed with the vector. The presence of a selectable marker sequence ensures growth of only those host cells which express the inserts. Typical selection maker polynucleotides encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the sequence encoding D-alanine racemase for Bacilli. The choice of the proper selectable marker will depend on the host cell and may be ascertained by those of skill in the art.

In some embodiments, the VGF biomolecule may be provided in a modified form or is provided in a combination with a distinct VGF peptide fragment to achieve increased potency.

The VGF biomolecule may function, for example, to increase insulin production or to modulate blood glucose levels, via a β-cell islet type. The VGF biomolecule may also function via a non-β-cell islet cell (e.g. glucagon-producing alpha-cells) thereby augmenting insulin release from the β-cell indirectly.

In some embodiments, methods of administering a VGF biomolecule to a cell, tissue, or patient are provided. A patient may include, for example, a human, mammal or animal. Examples of tissue include, but are not limited to, pancreatic tissue, islet tissue or a combination thereof. The cell may be, for example, an insulin producing cell such as a beta-cell. The patient may have one or more of hyperglycemia (e.g. chronic or acute), diabetes (e.g. Type I, Type II or gestational), complications or conditions associated with hyperglycemia and diabetes, pre-diabetes, Cushing's syndrome, acromelagy, hyperthyroidism, kidney infection, liver infection, pancreatic infection, or may be undergoing treatment with corticosteroids.

The VGF biomolecules may be effective for treating hyperglycemia or diabetes, increasing glucose stimulated insulin secretion, decreasing blood glucose concentration, improving acute glycemic control in response to an acute glucose challenge, improving chronic glycemic control, enhancing insulin secretion from islet beta cells, preserving or preventing or reducing a deterioration of islet beta-cell mass, islet beta-cell function or a combination thereof.

In some embodiments, methods are provided for treating or ameliorating hyperglycemia or complications or conditions associated therewith in a patient by administering a therapeutically effective amount of a VGF biomolecule. Hyperglycemia is a condition in which an excessive amount of glucose circulates in the blood above normal levels. Hyperglycemia may be determined by measuring the blood glucose concentration in a patient. Hyperglycemia may include, for example, a blood glucose concentration of at least about 100 mg/dL, at least about 110 mg/dL, at least about 120 mg/dL or at least about 125 mg/dL measured after 8 hours of fasting. Hyperglycemia may be acute or chronic. In some embodiments, hyperglycemia may be secondary to diabetes.

In some embodiments, methods are provided for modulating blood glucose concentration in a patient having an elevated blood glucose level. The method comprises administering a therapeutically effective amount of a VGF biomolecule. Modulating blood glucose concentration following administration of a VGF biomolecule means to effect a reduction in, or prevent an increase in, the level of circulating blood glucose in a patient, relative to a control patient that has not been administered with the VGF biomolecule. A patient in need of modulation of blood glucose concentrations includes a patient having elevated blood glucose concentrations. Such a patient may have a condition including one or more of hyperglycemia, diabetes, pre-diabetes, Cushing's syndrome, acromelagy, hyperthyroidism, kidney infection, liver infection, pancreatic infection, or be undergoing treatment with corticosteroids.

Blood glucose concentrations may be measured, for example, after fasting or postprandially. A fasting blood glucose level is the blood glucose concentration measured after 8 hours of fasting. An elevated fasting blood glucose level may include a blood glucose concentration of at least about 90 mg/dL, at least about 95 mg/dL, at least about 100 mg/dL, at least about 105 mg/dL, at least about 110 mg/dL, at least about 115 mg/dL, at least about 120 mg/dL, at least about 125 mg/dL, at least about 130 mg/dL, at least about 135 mg/dL, at least about 140 mg/dL, at least about 145 mg/dL, at least about 150 mg/dL, at least about 155 mg/dL, at least about 160 mg/dL, at least about 165 mg/dL, at least about 170 mg/dL, at least about 175 mg/dL, or at least about at least about 180 mg/dL.

A pre-diabetic patient is typically a patient having elevated blood glucose concentrations above normal levels, but who has not developed diabetes. A pre-diabetic patient may have a fasting blood glucose level of at least about 90 mg/dL, at least about 95 mg/dL, at least about 100 mg/dL, at least about 105 mg/dL, at least about 110 mg/dL, at least about 115 mg/dL, or at least about 120 mg/dL. In some embodiments, the pre-diabetic patient has a fasting blood glucose level of at least about 100 mg/dL.

A diabetic patient is typically a patient having diabetes such as Type I, Type II, or gestational diabetes, and may have a fasting blood glucose level of at least about 125 mg/dL, at least about 130 mg/dL, at least about 135 mg/dL, at least about 140 mg/dL, at least about 145 mg/dL, at least about 150 mg/dL, at least about 155 mg/dL, at least about 160 mg/dL, at least about 165 mg/dL, at least about 170 mg/dL, at least about 175 mg/dL, or at least about at least about 180 mg/dL.

In some embodiments, a method of enhancing glucose stimulated insulin secretion (GSIS) in a patient is provided. The method comprises administering to a patient a therapeutically effective amount of a VGF biomolecule. For example, a TLQP-21 polypeptide may be administered. In some embodiments, methods are provided for decreasing the blood glucose concentration by administration of a VGF biomolecule to a patient. The blood glucose levels may be modulated to be within normal range, such as below about 90 mg/dL, below about 85 mg/dL, below about 80 mg/dL, or below about 75 mg/dL after 8 hours of fasting.

In some embodiments, methods are provided for improving acute glycemic control in response to an acute glucose challenge in a patient by administration of a VGF biomolecule. Acute glycemic control means that blood glucose levels within one or two hours following an acute glucose challenge, such as may occur postprandially, are modulated to be closer to levels existing before the acute glucose challenge. Modulation includes effecting a reduction of or preventing an increase in the blood glucose level. The VGF biomolecule may be administered, for example, postprandially, to effect an improvement in acute glycemic control.

In some embodiments, methods are provided for enhancing GSIS by administration of a VGF biomolecule. Glucose stimulated insulin secretion may be increased at least about 1.2-fold, at least about 1.3-fold, at least about 1.4-fold, at least about 1.5-fold, at least about 1.6-fold, at least about 1.7-fold, at least about 1.8-fold, or at least about 2-fold compared with a patient, cell or tissue not having been administered with the VGF biomolecule.

In some embodiments, methods are provided for improving chronic glycemic control in a patient by administration of a VGF biomolecule. Chronic glycemic control includes a modulation of blood glucose levels over a period of time of at least several hours following administration of a VGF biomolecule. The time period may include fasting and non-fasting periods. In some embodiments, the improvements in chronic glycemic control persist for at least about 4 hours, at least about 8 hours, at least about 12 hours, at least about 16 hours, at least about 24 hours, at least about 2 days, at least about 3 days, at least about 4 days, at least about 5 days, at least about 6 days, at least about 1 week, at least about 2 weeks, at least about 3 weeks or at least about one month following administration of the VGF biomolecule. Chronic glycemic control may be achieved upon repeated administration of the VGF biomolecule. For example, administration may be carried out every 4 hours, every 8 hours, every 12 hours (four-times, three-times or twice daily), once daily, once weekly or once monthly.

In some embodiments, methods are provided for preserving islet beta cell mass, islet beta cell function or a combination thereof by administration of a VGF molecule. Islet dysfunction and loss of islet cell mass occur during the progression of insulin resistance toward overt Type II diabetes; individuals with Type II diabetes show 40-60% reductions in β-cell mass compared with healthy subjects. Preserving islet beta cell mass or function means that the mass of islet beta cells or their functions do not deteriorate, or deteriorate to a lesser extent, following administration of the VGF biomolecule, compared with a deterioration (or lack thereof) of islet beta cell mass or function that occurs in the absence of VGF biomolecule. Beta cell mass, function or a combination thereof may be preserved in a patient suffering from hyperglycemia, such as Type II diabetes, by administration of a VGF biomolecule. Administration of a VGF biomolecule may ameliorate the reduction in pancreatic beta cell mass function that is associated with Type II diabetes.

In some embodiments, methods are provided for reducing the onset of apoptosis in a cell, tissue or patient by administration of a VGF biomolecule. Administration of a VGF biomolecule may delay apoptosis in islet beta cells and thereby preserves islet beta cell mass and function.

The VGF polypeptides can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

In some embodiments, chemically modified derivatives of VGF polypeptides may provide additional advantages such as increased solubility, stability and circulating time of the polypeptide, or decreased immunogenicity (see U.S. Pat. No. 4,179,337, incorporated herein by reference in its entirety for any purpose). The chemical moieties for derivitization may be selected from water soluble polymers such as polyethylene glycol, ethylene glycol/propylene glycol copolymers, carboxymethylcellulose, dextran, polyvinyl alcohol and the like. The VGF polypeptides may be modified at random positions within the molecule, or at predetermined positions within the molecule and may include one, two, three or more attached chemical moieties.

The polymer may be of any molecular weight, and may be branched or unbranched. For polyethylene glycol, a molecular weight of between about 1 kDa and about 100 kDa (the term "about" indicating that in preparations of polyethylene glycol, some molecules will weigh more, some less, than the stated molecular weight) may be used. Other sizes may be used, depending on the desired therapeutic profile (e.g., the duration of sustained release desired, the effects, if any on biological activity, the ease in handling, the degree or lack of antigenicity and other known effects of the polyethylene glycol to a Therapeutic polypeptide or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

The polyethylene glycol may have a branched structure. Branched polyethylene glycols are described, for example, in U.S. Pat. No. 5,643,575 (incorporated by reference herein in its entirety for any purpose).

The polyethylene glycol molecules (or other chemical moieties) should be attached to the polypeptide with consideration of effects on functional or antigenic domains of the polypeptide. There are a number of attachment methods available to those skilled in the art, such as, for example, the method disclosed in EP 0 401 384 (coupling PEG to G-CSV), herein incorporated by reference; see also Mali et al., Exp. Hematol. 20:1028-1035 (1992), reporting pegylation of GM-CSF using tresyl chloride. For example, polyethylene glycol may be covalently bound through amino acid residues via reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. For therapeutic purposes, attachment at an amino group, such as attachment at the N-terminus or lysine group may be used.

As suggested above, polyethylene glycol may be attached to polypeptides via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the polypeptide.

Polypeptides chemically modified at the N-terminus may also be used. Using polyethylene glycol as an illustration of the present composition, one may select from a variety of polyethylene glycol molecules (by molecular weight, branching, etc.), the proportion of polyethylene glycol molecules to polypeptide (polypeptide) molecules in the reaction mix, the type of pegylation reaction to be performed, and the method of obtaining the selected N-terminally pegylated polypeptide. The method of obtaining the N-terminally pegylated preparation (i.e., separating this moiety from other monopegylated moieties if necessary) may be by purification of the N-terminally pegylated material from a population of pegylated polypeptide molecules. Selective polypeptides chemically modified at the N-terminus modification may be accomplished by reductive alkylation which exploits differential reactivity of different types of primary amino groups (lysine versus the N-terminal) available for derivatization in a particular polypeptide. Under the appropriate reaction conditions, substantially selective derivatization of the polypeptide at the N-terminus with a carbonyl group containing polymer is achieved.

As indicated above, pegylation of the VGF polypeptides of the invention may be accomplished by any number of means. For example, polyethylene glycol may be attached to the VGF polypeptide either directly or by an intervening linker. Linkerless systems for attaching polyethylene glycol to polypeptides are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of polypeptides without an intervening linker employs tresylated MPEG, which is produced by the modification of monmethoxy polyethylene glycol (MPEG) using tresylchloride ($ClSO_2CH_2CF_3$). Upon reaction of polypeptide with tresylated MPEG, polyethylene glycol is directly attached to amine groups of the polypeptide. Thus, the invention includes polypeptide-polyethylene glycol conjugates produced by reacting VGF polypeptides with a polyethylene glycol molecule having a 2,2,2-trifluoreothane sulphonyl group.

Polyethylene glycol can also be attached to polypeptides using a number of different intervening linkers. For example, U.S. Pat. No. 5,612,460, the entire disclosure of which is incorporated herein by reference for any purpose, discloses urethane linkers for connecting polyethylene glycol to polypeptides. Polypeptide-polyethylene glycol conjugates wherein the polyethylene glycol is attached to the polypeptide by a linker can also be produced by reaction of polypeptides with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to polypeptides are described in International Publication No. WO 98/32466, the entire disclosure of which is incorporated herein by reference.

The number of polyethylene glycol moieties attached to each VGF polypeptide (i.e., the degree of substitution) may also vary. For example, the pegylated polypeptides of the invention may be linked, on average, to 1, 2, 3, 4, 5, 6, 7, 8, 9, 10, 12 or 15, or more polyethylene glycol molecules. Similarly, the average degree of substitution within ranges such as 1-3, 2-4, 3-5, 4-6, 5-7, 6-8, 7-9, 8-10, 9-11, 10-12, or 13-15 polyethylene glycol moieties per polypeptide molecule. Methods for determining the degree of substitution are discussed, for example, in Delgado et al., Crit. Rev. Thera. Drug Carrier Sys. 9:249-304 (1992).

Another form of polypeptide modification that may result in improved pharmacological properties is glycosolation. Glycosylation of proteins is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to proteins comprising at least one follistatin domain is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original protein (for O-linked glycosylation sites).

Another means of increasing the number of carbohydrate moieties on proteins is by chemical or enzymatic coupling of glycosides to the amino acid residues of the protein. These procedures are advantageous in that they do not require production of the GDF peptide inhibitor in a host cell that has glycosylation capabilities for N- or O-linked glycosylation.

Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston (1981) CRC Crit. Rev. Biochem., 22: 259-306.

In some embodiments, the VGF biomolecule is provided with a controlled release polymer that may be selected from bulk erosion polymers (e.g., poly(lactic-co-glycolic acid) (PLGA) copolymers, PLGA polymer blends, block copolymers of PEG, and lactic and glycolic acid, poly(cyanoacrylates)); surface erosion polymers (e.g., poly(anhydrides) and poly(ortho esters)); hydrogel esters (e.g., pluronic polyols, poly(vinyl alcohol), poly(vinylpyrrolidone), maleic anhydride-alkyl vinyl ether copolymers, poly(2-hydroxyethyl methacrylate) (pHEMA), methacrylic acid (MAA), blends of pHEMA and MAA, cellulose (e.g., carboxymethylcellulose), hyaluronan, alginate, collagen, gelatin, albumin, and starches and dextrans) and composition systems thereof; or preparations of liposomes or microspheres. Such compositions may influence the physical state, stability, rate of in vivo release, and rate of in vivo clearance of the present proteins and derivatives. The optimal pharmaceutical formulation for a VGF biomolecule will be determined by one skilled in the art depending upon the route of administration and desired dosage.

In some embodiments a therapeutically effective amount of a VGF biomolecule is administered to the patient. The VGF biomolecule may be provided with an appropriate pharmaceutical carrier. While it is possible for the VGF biomolecule to be administered alone, the VGF biomolecule may be presented as a pharmaceutical composition (e.g., formulation) together with one or more pharmaceutically-acceptable carriers, adjuvants, excipients, diluents, fillers, buffers, stabilizers, preservatives, lubricants, or other materials well known to those skilled in the art and optionally other therapeutic or prophylactic agents. These carriers may include liposomes and microspheres. In some embodiments, the carrier is formulated to protect the VGF biomolecule from degradation and to facilitate delivery to the target site. For example, for oral delivery, a carrier is used to prevent degradation of the VGF biomolecule in the gastrointestinal system, to facilitate its absorption into the blood stream, to target delivery to the desired site, or a combination thereof.

The term pharmaceutically acceptable pertains to compounds, materials, compositions, and/or dosage forms which are, within the scope of sound medical judgment, suitable for use in contact with the tissues of a subject (e.g., patient, human or other animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Exemplary carriers, excipients, diluents etc. can be found in standard pharmaceutical texts, for example, Remington's Pharmaceutical Sciences, 18th edition, Mack Publishing Company, Easton, Pa., 1990. Pharmaceutically acceptable carriers and/or diluents include, for example, any and all conventional solvents, dispersion media, fillers, solid carriers, aqueous solutions, coatings, antibacterial and antifungal agents, isotonic and absorption delaying agents, and the like. Except insofar as any conventional media or agent is incompatible with the active VGF biomolecule or other active component, use thereof in the pharmaceutical compositions is contemplated. Supplementary active ingredients may also be incorporated into the compositions.

The formulations will conveniently be presented in unit dosage form and will be prepared by any method well known in the art of pharmacy. Such methods include the step of bringing into association the active compound with the carrier which constitutes one or more accessory ingredients. In general, the formulations will be prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations for oral administration (e.g., by ingestion) may be presented, for example, as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations for topical administration (e.g., transdermal, intranasal, ocular, buccal, and sublingual) may be formulated, for example, as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. In addition, a formulation may be added to a conventional bandage, e.g. to a gauze portion that contacts the wound, as an antimicrobial agent.

Formulations for topical administration in the mouth include, for example, losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a liquid carrier.

Formulations for topical administration to the eye also include, for example, eye drops wherein the active compound is dissolved or suspended in a carrier, especially an aqueous solvent for the active compound.

Formulations for topical administration via the skin include, for example, ointments, creams, and emulsions. When formulated in an ointment, the active compound may optionally be employed with either a paraffinic or a water-miscible ointment base. Alternatively, the active compound may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. A hydrophilic emulsifier may be included together with a lipophilic emulsifier which acts as a stabilizer. Also, both an oil and a fat may be included. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers include, for example, Tween 60, Span 80, cetostearyl alcohol, myristyl alcohol, glyceryl monostearate and sodium lauryl sulphate. The choice of oils or fats for the formulation may be based on achieving the desired cosmetic properties. Thus the cream may be a non-greasy, non-staining and washable product with a consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Formulations for nasal administration, wherein the carrier is a solid, include, for example, a coarse powder having a particle size, for example, in the range of about 20 to about 500 microns which is administered in the manner in which snuff is taken, i.e., by rapid inhalation through the nasal passage from a container of the powder held close up to the nose. Nasal formulations wherein the carrier is a liquid for administration as, for example, nasal spray, nasal drops, or by aerosol administration by nebulizer, include, without limitation, aqueous or oily solutions of the active compound.

Formulations for administration by inhalation include, for example, those presented as an aerosol spray from a pressurized pack, with the use of a propellant, such as dichlorodifluoromethane, trichlorofluoromethane, dichoro-tetrafluoroethane, carbon dioxide, or other gases.

Formulations for rectal administration may be presented, for example, as a suppository with a suitable base comprising, for example, cocoa butter or a salicylate.

Formulations for vaginal administration may be presented, for example, as pessaries, tampons, creams, gels, pastes, foams or spray formulations containing in addition to the active compound, such carriers as are known in the art to be appropriate.

Formulations used for parenteral administration (e.g., by injection, including cutaneous, subcutaneous, intramuscular, intravenous and intradermal), include, for example, aqueous and non-aqueous isotonic, pyrogen-free, sterile injection solutions which may contain anti-oxidants, buffers, preservatives, stabilizers, bacteriostats in addition to the active compound, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Aqueous preparations may be formulated using dispersing or wetting agents and suspending agents. A sterile injectable preparation may be formulated as a sterile injectable solution or suspension in a nontoxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils may be employed as a solvent or suspending medium. For this purpose, any bland fixed oil may be employed including synthetic mono- or di-glycerides. In addition, fatty acids such as oleic acid may be used in the preparation of injectables. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active VGF biomolecules, and compositions comprising the active VGF biomolecules, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. Generally the dosage will be to achieve local concentrations at the site of action which achieve the desired effect without causing substantial harmful or deleterious side-effects.

The amount of VGF biomolecules of the invention administered to have a therapeutic effect will depend, at least in part, on their half-life and bioavailability, which may be altered by those of skill in the art, for example, by pegylation or glycosolation as described herein, or using other techniques known in the art. The VGF biomolecule is suitably administered in therapeutically effective amounts. A therapeutically effective amount means that amount necessary at least partly to attain the desired effect, ameliorate the symptoms of, or to delay the onset of, inhibit the progression of, or halt altogether, the onset or progression of the disease or condition being treated.

The VGF biomolecules may be administered to a patient in an amount of at least about 0.01 mg/kg/day, at least about 0.02 mg/kg/day, at least about 0.03 mg/kg/day, at least about 0.05 mg/kg/day, at least about 0.075 mg/kg/day, at least about 0.1 mg/kg/day, at least about 0.2 mg/kg/day, at least about 0.3 mg/kg/day, at least about 0.4 mg/kg/day, at least about 0.5 mg/kg/day, at least about 0.6 mg/kg/day, at least about 0.07 mg/kg/day, or at least about 0.08 mg/kg/day, or at least about 0.1 mg/kg/day, or at least about 0.2 mg/kg/day, or at least about 0.5 mg/kg/day, or at least about 1.0 mg/kg/day, and less than about 150 mg/kg/day, less than about 125 mg/kg/day, less than about 100 mg/kg/day, less than about 90 mg/kg/day, less than about 80 mg/kg/day, less than about 70 mg/kg/day, less than about 60 mg/kg/day, less than about 50 mg/kg/day, less than about 40 mg/kg/day, less than about 30 mg/kg/day, less than about 20 mg/kg/day, less than about 10 mg/kg/day, less than about 8 mg/kg/day, less than about 5 mg/kg/day, less than about 4 mg/kg/day, less than about 3 mg/kg/day, or less than about 2 mg/kg/day. These amounts may also be suitably administered two, three or four times per day, every second, third, fourth, fifth or sixth day, and/or weekly, biweekly or monthly.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

Delivery systems may include, for example, sustained release delivery systems. Sustained release delivery systems include those which can provide for release of the active component in sustained release pellets or capsules. Sustained release delivery systems include, but are not limited to: (a) erosional systems in which the active component is contain within a matrix, and (b) diffusional systems in which the active component permeates at a controlled rate through a polymer. Specific controlled release compositions are available from the following suppliers: DepoTech Corp., San Diego, Calif. (Depofoam™, a multivesicular liposome) and Alkermes, Inc., Cambridge, Mass. (ProLease™ a PLGA microsphere).

In certain embodiments, the VGF biomolecule is administered in conjunction or combination with one or more other therapeutic agents, for example in a treatment regime. The VGF biomolecule may be administered in a regime with at least one or more therapeutic agents. Therapeutic agents that may be co-administered with the VGF biomolecule include one or more of biguanides (e.g. metformin), meglitinides (e.g. repaglinide, nateglinide), sulfonylureas, thiazolidinediones, alpha glucosidase inhibitors, dipeptidyl peptidase inhibitors, ergot alkaloids, insulin, incretin mimetics, and amylin analogues.

It will be apparent to those of skill in the art that variations may be applied to the compositions and methods described herein and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following non-limiting examples are purely illustrative.

EXAMPLES

Analytical Techniques Used in Examples 1 to 7

Cell Culture and Reagents

832/3 and 832/13 cells derived from the parental INS-1 cell line were cultured as previously described (REF-Hohmeier/Wolheim). Pancreatic islets were isolated from male Sprague-Dawley rats according to standard procedures (See, e.g., Ronnebaum et al., (2006) J. Biol. Chem. 281: 30593-30602). For cell culture experiments, TLQP-21 was purchased from Phoenix Pharmaceuticals. For animal studies, TLQP-21 was synthesized by GenScript Corporation. AQEE-30 was a kind gift of Dr. Yun-Ping (Merck Research Laboratories).

Human VGF cDNA was purchased from Open Biosystems and subcloned into pAC.CMV using PCR engineered restriction sites. Recombinant adenovirus was generated as previously described (REF). Adenoviruses expressing Nkx6.1, Pdx-1, GFP, beta-galactosidase have been described elsewhere (REF). Cells were transduced with adenovirus at a multiplicity of infection of 10-50 of for 18 hrs and assayed 72 hr post-infection. Pools of 100 islets were transduced with ~2×10$^7$ IFU/mL adenovirus (multiplicity of infection (moi) ~100-200) for 18 hrs and assayed 72 hrs post-infection.

Male Wistar rats were purchased from Harlan and maintained on standard chow (XX; Research Diet). Male Zucker Diabetic Fatty (fa/fa) rats were purchased from Charles River Laboratories and maintained on standard chow (YY; Research Diets). All animal protocols were approved by the Duke University Institutional Animal Use and Care Committee For generation of polyclonal antisera, a 15 residue peptide corresponding to rat VGF 556-570 (amino acid sequence) containing an amino-terminal cysteine (GenScript Corporation) conjugated to KLH was used to immunize rabbits (Cocalico Biologicals, Inc.). Antiserum was affinity purified using the immunizing peptide coupled to Sulfolink gel resin (Pierce).

Glucose-Stimulated Insulin Secretion

Islets: 3 groups of 20 islets were washed with phosphate-buffered saline (PBS) and incubated in secretion assay buffer (SAB; 114 mM NaCl, 4.7 mM KCl, 1.2 mM KH$_2$HPO$_4$, 1.16 mM MgSO$_4$, 25 mM HEPES pH 7.2, 2.5 mM CaCl$_2$, 0.2% bovine serum albumin (Gibco), 25.5 mM NaHCO$_3$) containing 2.5 mM Glc for 1 hr at 37° C. Insulin was collected by static incubation in SAB containing 2.5 mM Glc for 1 hr at 37° C. (basal) followed by incubation in SAB containing 16.7 mM Glc for 1 hr (stimulatory). Secretagogues (20 nM exendin-4, TLQP-21, AQEE-30) were added where indicated. Islets were washed in PBS and collected by centrifugation.

Islets were lysed in RIPA buffer containing 5 mM EDTA and total protein determined by BCA (Pierce). Insulin was measured from SAB using the Coat-a-Count kit (Siemens). Insulin content was determined from a 1:100 dilution of total protein.

832/3 cells were plated in triplicate per condition in 12-well dishes and assayed at confluence. Cells were washed in SAB buffer and pre-incubated for 1.5 hr in SAB containing 2.5 mM Glc. Insulin was collected by static incubation in SAB containing 2.5 mM Glc for 2 hrs at 37° C. (basal) followed by incubation in SAB containing 12 mM Glc for 2 hrs (stimulatory). Secretagogues (20 nM exendin-4, TLQP-21, AQEE-30) were added where indicated. Cells were washed in PBS, collected by centrifugation, and lysed in 50 uL RIPA containing 5 mM EDTA. Total protein was determined by BCA (Pierce). Insulin was measured from SAB using the Coat-a-Count kit (Siemens). Insulin content was determined from a 1:500 dilution of total protein.

Immunoblot Analysis

Pools of 80 islets were washed in phosphate-buffered saline and lysed in 30 uL RIPA buffer containing 5 mM EDTA and Halt protease inhibitor cocktail (Pierce). 20-30 ug of clarified cell lysate was resolved on 4-12% NuPAGE gels (Invitrogen) and transferred to polyvinylidene fluoride (PVDF) membrane. Membranes were probed with diluted antibodies raised against Nkx6.1 (Iowa Developmental Hybridoma Bank), Pdx-1 (Abcam), GFP (Abcam), gamma-tubulin (Sigma), and VGF (this paper). Sheep anti-mouse (1:10,000) and goat-anti-rabbit (1:10,000) antibodies (GE Healthcare) coupled to peroxidase were used to detect primary antibodies. Blots were developed with ECL advance reagent (GE Healthcare).

Quantitative RT-PCR

For primary rat islets, RNA was harvested from 20 islets using the RNeasy microkit (Qiagen). For 832/3 cells, RNA was harvested using the RNeasy minikit (Qiagen). Approximately 500-1000 ng of RNA was used for cDNA synthesis in a 20 uL iScript reaction (Bio Rad). Real-time PCRs were performed using the ABI 7000 s sequence detection system and software (Applied Biosystems). Human VGF primers used were a TaqMan-based Assay on Demand (Applied Biosystems). All other primer sequences are available upon request.

cAMP Level Determination

Primary rat islets and 832/3 cells were prepared as stated for insulin secretion measurements except the incubation at stimulatory glucose was for 30 min in the presence of 0.1 mM isobuytlmethylxanthine (IBMX). Rat islets were rapidly transferred to 0.2 mL of ice-cold 80% ethanol and stored at −80° C. until assayed. Samples were evaporated to dryness and assayed using the cAMP EIA kit from Biomedical Technologies, Inc. using acetylation protocol. For 832/3 cells, the secretion buffer was removed and rapidly replaced with 0.5 mL of 80% ethanol. Cells were stored at −80° C. until assayed. 0.2 mL of sample was evaporated to dryness and assayed for cAMP using the non-acetylation protocol.

Intraperitoneal Glucose and Insulin Tolerance Tests

For i.p. glucose tolerance tests, overnight (12 hr) fasted rats were injected i.p. with a 1 g/kg or 2 g/kg glucose bolus as indicated. Blood glucose was monitored using a glucometer (Becton Dickinson). Blood was collected from the saphenous vein in Micovette capillary tubes coated with EDTA (Sarstedt) and plasma separated by centrifugation. Insulin levels were determined using a rat/mouse insulin ELISA (Millipore). For i.p. insulin tolerance tests, ad libitum fed animals were injected i.p. with 1 U/kg Humulin (Eli Lily). As indicated, 30 min prior to the glucose bolus, animals receive i.p. injections of saline or TLQP-21 dissolved in saline.

Histology and In Situ Immunofluorescence

Pancreata were immersion fixed in neutral-buffered formalin followed by paraffin embedding, orienting longitudinally along the head-tail axis. Sections (5 μm) were deparaffinized in xylene and rehydrated using a graded ethanol series. Antigen retrieval was performed using a sodium citrate buffer (Dako) according to the manufacturer's protocol. For insulin staining, slides were incubated overnight with guinea pig anti-insulin (Dako) followed by detection with an AlexaFluor 488 conjugated goat anti-guinea pig secondary antibody. Slides were counterstained with DAPI. Images were captured and analyzed using OpenLab software. β-cell mass was determined as the total insulin staining area divided by the total cross-sectional tissue area per slide. Hoescht-eosin staining of adjacent tissue sections was used to determine total tissue section area. For detection of β-cell apoptosis, sections were processed for terminal deoxynucleotide transferase-mediated 2'-deoxyuridine 5'-triphosphate nick-end labeling (TUNEL) staining using the In Situ Cell Death Detection Kit TMR red (Roche Diagnostics) according to the manufacturer's protocol. The data were quantified as the total number of TUNEL staining, insulin staining double positive cells relative to the total number of islets counted. A minimum of 4 slides per animal spaced 75-100 μm apart per pancreas was used for β-cell mass and TUNEL staining quantification.

Chronic Peptide Treatment Study 7 wk old male Zucker Diabetic Fatty (fa/fa) rats were randomly assigned to 1 of 3 groups receiving TLQP-21, a scrambled peptide of identical amino acid composition to TLQP-21, or the vehicle saline. 5 mg/kg peptide or an equivalent volume of saline was injected on alternating days for 4 wks. Ad libitum fed blood glucose was measured in the morning and blood collected weekly via the saphenous vein as noted elsewhere.

Flow Cytometry

Pools of 50 islets were treated with DMSO, etoposide (0.2 mM) or camptothecin (10 μM) for 72 hrs as indicated. Islets were co-incubated with peptide (50 nM TLQP-21, 50 nM exendin-4), H89 (concentration), and/or LY294002 (concentration) where indicated. Islets were dispersed using 0.05% trypsin/EDTA (Sigma) diluted 1:1 with cell dissociation buffer (Sigma) for 5-10 min at 37 C following gentle pipetting. Islets were recovered by centrifugation and stained with FITC-conjugated Annexin V and propidium iodide (Roche) according to the manufacturer's specifications. Data were collected using a FACScan analyzer and analyzed using WinMDI 2.9 software.

Statistical Analysis

Data presented in Examples 1 to XX show the mean±S.E.M. and were analyzed by the paired, Student's t test or by ANOVA with Tukey's post-hoc analysis for multiple group comparisons for statistical significance.

Example 1

Overexpression of Nkx6.1, but not Pdx-1 Enhances Glucose-Stimulated Insulin Secretion Nkx6.1 is a homeobox transcription factor that stimulates rodent and human islet β-cell replication and provides an improvement in islet function when overexpressed. Both direct (transcriptional) and indirect upregulation of cell cycle genes, particularly cyclins A1, B1 and E and Cdk-1 and -2 occurs. Overexpression of Nkx6.1 in isolated rat islets enhances glucose-stimulated insulin secretion (GSIS). Pdx-1 is another prominent β-cell transcription factor. Suppression of Pdx-1 in isolated rat islets strongly diminishes GSIS. Mutations inactivating Pdx-1 in humans result in the dominant heritable form of maturity onset diabetes of the young (MODY4).

We examined the ability of Nkx6.1 and Pdx-1 overexpression to enhance insulin release in primary rat islets. (FIG. 1) Recombinant adenoviruses expressing hamster Nkx6.1 cDNA (AdCMV-Nkx6.1) or mouse Pdx-1 cDNA (AdCMV-Pdx-1) relative to a control adenovirus expressing GFP (Ad-CMV-GFP) were used. Nkx6.1 and Pdx-1 protein levels were found to be elevated by almost 10-fold (FIG. 1D). Nkx6.1 overexpression (AdCMV-Nkx6.1) improved islet function, resulting in a 40% increase in GSIS without compromising basal insulin release (FIG. 1A). Notably, Nkx6.1 overexpression was not accompanied by changes in insulin gene expression, insulin content, glucokinase, or GLUT2 expression. In contrast to the effects of Nkx6.1, a similar overexpression level of Pdx-1 was not sufficient to enhance GSIS (FIG. 1A); rather insulin release was unaffected in AdCMV-Pdx-1 treated islets compared to control (AdCMV-GFP) islets.

From the observation in FIG. 1A, we postulated that genes specifically regulated by Nkx6.1 but not Pdx-1 contribute to the Nkx6.1-mediated increase in GSIS. We compared cDNA microarray analysis from rat islets overexpressing Nkx6.1 (AdCMV-Nkx6.1) as compared to a control gene, beta-galactosidase (AdCMV-bgal) with a cDNA microarray study performed using rat islets overexpressing Pdx-1 (AdCMV-Pdx-1). Genes that were increased or decreased 2-fold or greater by Nkx6.1 and not Pdx-1 or the beta-galactosidase control were identified as potential Nkx6.1 target genes that may regulate or influence islet β-cell function. We identified the nerve growth factor-inducible gene VGF as the most highly upregulated gene following Nkx6.1 overexpression yet unchanged by Pdx-1 overexpression.

To confirm the results of the microarray data, we examined both the mRNA and protein expression levels of VGF following Nkx6.1 or Pdx-1 overexpression in rat islets. As shown in FIG. 1C, we observed a 25-fold upregulation of VGF mRNA in rat islets in response to overexpression of Nkx6.1 (AdCMV-Nkx6.1), but not Pdx-1 (AdCMV-Pdx-1) or a GFP control (AdCMV-GFP). To ascertain the impact of Nkx6.1 overexpression on VGF protein levels, we raised polyclonal antisera to a C-terminal portion of the rat VGF protein (amino acids 556-570). Using purified antisera, we observed a robust increase in pro-VGF expression following treatment of islets with AdCMV-Nkx6.1, but not AdCMV-Pdx-1 or the GFP control virus (AdCMV-GFP) (FIG. 1B). These data are the first to directly link a transcription factor to VGF gene expression.

Example 2

VGF Expression Levels Directly Correlate with Islet Beta-Cell Function

To examine whether there is a direct role for VGF in regulating insulin secretion from the islet β-cell, we used both overexpression and suppression studies in primary rat islets and insulinoma cells. To determine if VGF is required for normal insulin secretion, we used two distinct siRNAs to suppress VGF in the rat beta-cell line 832/13. As shown in FIG. 2A, an 80% reduction of VGF protein (FIGS. 2B, D), resulted in a significant impairment in GSIS. To further explore the deficiency in insulin release, we also examined insulin release in response to direct membrane depolarization using both elevated K+(35 mM KCl) and the sulfonylurea tolbutamide. Under both conditions tested, insulin release was markedly impaired following VGF suppression (FIG. 2C).

To measure VGF overexpression enhancement on GSIS we generated a recombinant adenovirus containing the human VGF cDNA and used comparable overexpression values as seen following Nkx6.1-mediated induction of endogenous VGF (FIG. 1C vs. FIGS. 3C, F). In FIG. 3, we examined the effects of VGF overexpression in both rat islets and the robustly glucose responsive 832/3 cell line derived from the parental INS-1 beta cell line. 832/3 cells are incretin sensitive presenting with a GLP-1 response similar to isolated rat islets (FIGS. 4B, D). As shown in FIG. 3A, overexpression of VGF in primary rat islets resulted in a large increase in GSIS (16.7 mM Glc), without compromising basal insulin secretion (2.5 mM Glc) or elevating insulin content (FIG. 3B). Similarly, VGF overexpression in 832/3 cells resulted in a dose-dependent increase in glucose-stimulated insulin release (FIG. 3D), again, without affecting basal insulin secretion (2.5 mM Glc) or insulin content (FIG. 3E). Nkx6.1 levels were found not to be affected by manipulation of VGF expression. These data demonstrate that VGF overexpression is sufficient to recapitulate the Nkx6.1-mediated augmentation of islet β-cell function.

Example 3

The C-Terminal VGF Peptide TLQP-21 Potentiates GSIS in Rat Islets

Two C-terminal VGF peptides, TLQP-21 and AQEE-30, have been previously documented to play distinct roles in the central nervous system. To ascertain if either of the C-terminal VGF peptides, TLQP-21 or AQEE-30 were able to increase GSIS as observed with VGF overexpression, we investigated the impact of acute administration of these peptides on insulin secretion in 832/3 cells and primary rat islets. In these experiments, addition of the GLP-1 receptor analog, exendin-4 was used as a positive control for potentiation of GSIS. As shown in FIG. 4A, addition of TLQP-21 to rat islets resulted in a dose-dependent increase in GSIS with modest effects observed at 500 μM and a maximal 35% increase in GSIS occurring by 50 nM.

In comparison, 20 nM exendin-4 enhanced GSIS 1.8-fold. Similar to the GLP-1 receptor agonist, TLQP-21 potentiated insulin release only at stimulatory glucose concentrations and did not raise basal insulin secretion. These results are consistent with the observed effect for VGF overexpression in rat islets (FIG. 3A). In contrast, 832/3 cells were unresponsive to TLQP-21 at concentrations that clearly augment insulin release in isolated rat islets (FIG. 4B vs. FIG. 4A). These results are in contrast to the shared effects of VGF overexpression in rat islets and 832/3 cells (FIGS. 3A, D). Long-term (up to 72 hr) administration and/or higher concentrations of TLQP-21 (up to 0.1 mM) failed to potentiate GSIS in 832/3 cells demonstrating that the lack of response was not simply due to incubation time or amount of TLQP-21 present. Similar to 832/3 cells, TLQP-21 did not affect insulin release in the parental INS-1 cell line. In FIGS. 4C and 4D, we examined a second C-terminal VGF peptide, AQEE-30, for its ability to potentiate GSIS. In both rat islets and 832/3 cells, AQEE-30 was unable to augment GSIS. Additionally, we found that AQEE-30 and TLQP-21 did not synergistically enhance GSIS in 832/3 cells. These results identify TLQP-21 as a relevant VGF-derived ligand sufficient for the potentiation of GSIS in rat islets.

Example 4

TLQP-21 Elevates cAMP Levels in Primary Islets

To investigate the operative receptor signaling pathway utilized by TLQP-21 to potentiate GSIS in rat islets, we examined changes in cAMP levels upon treatment of islets and 832/3 cells with TLQP-21 at stimulatory glucose concentrations (16.7 mM and 12 mM, respectively). We postulated that TLQP-21 may function through a G-protein/adenylate cyclase-coupled receptor system analogous to the incretin hormones GLP-1 and GIP and the vagal peptides, PACAP and VIP. Exendin-4 was used as a potent physiological ligand for increased cAMP production. As shown in FIG. 5A, treatment of rat islets with TLQP-21 resulted in a 2-fold increase in cAMP levels, whereas exendin-4 yielded an almost 3-fold increase in cAMP. These values are consistent with the more potent effects of exendin-4 on GSIS relative to TLQP-21 (FIG. 4A). These results suggest that similar to the incretin hormones, GLP-1 and GIP, TLQP-21 also signals through a G-protein-coupled receptor system. In 832/3 cells, TLQP-21 failed to elevate cAMP (FIG. 5B), consistent with the lack of effect of this peptide on insulin release (FIG. 4B). Thus, the inability of 832/3 cells to respond to TLQP-21 was due to a lack of receptor-coupled signaling rather than TLQP-21 signaling falling short of a necessary threshold of cAMP accumulation to potentiate GSIS.

Example 5

TLQP-21 Reduces Glycemic Excursion Through Increased Insulin Release In Vivo To investigate the effects of TLQP-21 in whole animals, we examined the impact of TLQP-21 administration on glucose and insulin levels following a glucose challenge in male Wistar rats. Overnight fasted animals were injected (i.p.) with 4.5 mg/kg TLQP-21 or vehicle saline at 30 minutes prior to a 1 g/kg glucose bolus (FIG. 6A-C). Animals receiving TLQP-21 exhibited a ~20% reduction in blood glucose at the peak glucose level (20 min) (FIG. 6A). This reduction persisted beyond 60 minutes post-glucose challenge. Area under the curve (AUC) analysis demonstrated a 25% decrease in glycemic excursion following TLQP-21 administration (FIG. 6C). The TLQP-21 mediated reduction in blood glucose was accompanied by a 25% increase in plasma insulin levels (FIG. 6B) demonstrating that in vivo, TLQP-21 can potentiate insulin release. These values are consistent with the observed effects of TLQP-21 on GSIS potentiation in isolated rat islets (FIG. 4A).

We next examined whether TLQP-21 had any impact on overall insulin sensitivity. PACAP and VIP, which are potent islet secretagogues, diminish insulin sensitivity via release of counter-regulatory peptides such as glucagon. Two independent doses of TLQP-21 relative to vehicle saline were administered to ad libitum fed rats followed by a 1 U/kg insulin injection (FIG. 6D). In these animals, the decrement in blood glucose following insulin challenge was similar between control and treated groups indicating TLQP-21 does not diminish insulin sensitivity. We further explored the activity of TLQP-21 at 3 independent doses (5 mg/kg, 1 mg/kg and 0.5 mg/kg) during a (2 g/kg) glucose tolerance test (FIGS. 6E, F). We observed a dose dependent reduction in glycemic excursion upon TLQP-21 treatment with modest activity still present at the 1 mg/kg dose and the 0.5 mg/kg dose falling just short of statistical significance (pvalue≤0.06). These studies demonstrate that both in isolated islet cultures as well as in whole animals, the VGF peptide TLQP-21 is a potent β-cell secretagogue.

Example 6

TLQP-21 Improves Glycemic Control and Preserves Islet Cell Mass in a Rodent Model of T2D To determine the potential for TLQP-21 as a treatment for Type II diabetes (T2D), we first examined the effects of an acute TLQP-21 treatment on glucose tolerance in a genetic model of T2D, the leptin receptor deficient Zucker Diabetic Fatty (ZDF; fa/fa) rat. For this experiment, we performed glucose tolerance tests on (10 wk old) pre-diabetic ZDFs, which typically exhibit impaired glucose tolerance (IGT), impaired fasting glucose (IFG) and hyperinsulinemia. Overnight fasted animals (n=6 per group) were injected i.p. (downward facing arrow) with either 4.5 mg/kg TLQP-21 or saline control at 30 minutes prior to a glucose bolus (FIG. 7). Vehicle (saline) control animals were glucose intolerant with blood glucose still above 200 mg/dl 2 hrs following glucose administration (FIG. 7A). In contrast, animals receiving TLQP-21 exhibited a reduction in glycemic excursion suggesting a rapid normalization of glucose tolerance. Moreover, we also observed a significant decrease in fasting glucose levels 30 min post treatment with the VGF peptide, TLQP-21. Note that this was not observed in healthy Wistar rats (FIGS. 6A, E).

To further evaluate the potential for TLQP-21 as anti-diabetogenic agent, we performed a chronic (4 wk) treatment study in male ZDF (fa/fa) rats. Male ZDF rats are a well-characterized model of islet β-cell failure that occurs during the progression of insulin resistance towards the pathogenic state of overt diabetes. In this study, 7 wk old animals were divided into 3 groups receiving either TLQP-21, a scrambled peptide of identical amino acid sequence to TLQP-21 (SCR), or vehicle saline. At this age (7 wks), the animals have yet to present with hyperglycemia (FIG. 8A; first time point). Animals received injections (i.p.) on alternating days of 5 mg/kg peptide (or equivalent volume of saline) for 4 wks. As shown in FIG. 8A, treatment of ZDF rats with TLQP-21 yielded a trend toward lower glucose in the ad libitum fed state reaching statistical significance by the conclusion of the study. At this time point, which represents the onset of overt diabetes in control animals, fed blood glucose of animals receiving TLQP-21 was on average 150 mg/dl lower than either of the two control groups. No changes in body mass were observed. An improvement in glucose tolerance with TLQP-21 treatment was also noted; in these animals there was a marked reduction in glycemic excursion following a glucose challenge, whereas control animals (SCR and saline) were unable to significantly lower their blood glucose by 2 hrs post glucose challenge (FIG. 8C). The animals did not receive peptide within 24 hrs of the glucose tolerance test. In addition, fasting blood glucose (t=0 min) was ~150 mg/dl lower in TLQP-21 treated animals (FIG. 8C, t=0 min). Accordingly, there was a glucose-lowering effect of the VGF derived peptide TLQP-21 in a rodent model of islet dysfunction.

To determine if the glucose-lowering effect of TLQP-21 treatment was accompanied by an improvement and/or preservation of islet β-cell function, we examined plasma insulin levels from ad libitum fed animals sampled throughout the treatment study as well as fasting levels sampled at the conclusion of the study. In the ad libitum fed state, plasma insulin levels were sustained at a hyperinsulinemic level in animals receiving TLQP-21 as compared to control animals that exhibited a continued decline in circulating insulin (FIG. 8B).

This decline in insulin was consistent with the continued rise in hyperglycemia. Plasma insulin levels obtained from fasted animals sampled at the end of the study also showed significantly higher levels of circulating insulin in TLQP-21 treated animals than either of the control groups (FIG. 8D).

To ascertain whether the improvement in glycemic control and overall maintenance of a hyperinsulinemic state in the TLQP-21 treated animals was due to a preservation of islet β-cell mass, and to directly explore possible effects of TLQP-21 on islet β-cell mass, we performed a histological examination of pancreata from the 3 treatment groups of ZDF rats. Quantification of insulin staining area revealed a marked difference in overall β-cell mass between the animals receiving TLQP-21 and the two control groups. TLPQ-21 treated animals had 40% higher β-cell mass relative to control animals. Analysis of DNA fragmentation via TUNEL staining showed that the difference in islet β-cell mass was due, at least in part, to a decrease in β-cell death in TLQP-21 treated animals.

Example 7

TLQP-21 Partially Protects Islets from Apoptosis

FIG. 8 shows that preservation of islet β-cell mass correlates with reduced β-cell death in an animal model of islet dysfunction. To determine whether TLQP-21 may possess anti-apoptotic activity with respect to the islet cells, we evaluated the induction of apoptosis using the topoisomerase I inhibitors, etoposide and camptothecin, in isolated rat islets in the presence or absence of the VGF peptide TLQP-21. Exendin-4 and forskolin were used as positive controls for protection from apoptosis; notably, both of these agents are potent inducers of adenylyl cyclase activity and the downstream PKA pathway Annexin V staining was used as a surrogate for the induction of apoptosis. In FIG. 9, 72 hr treatment of isolated islets with etoposide resulted in 35% of the islet cells staining positive for Annexin V, which was an increase in 18% over untreated (DMSO) control cells. Co-culture of islets with TLQP-21 resulted in 24% of islet cells staining Annexin V positive, a decrease in 69% relative to etoposide only treated cells. A comparable level of protection was achieved with exendin-4, whereas forskolin was completely protective against etoposide-mediated apoptosis.

Example 8

Clinical Lab Testing

Clinical lab tests will use a cohort of patients identified as having Type II diabetes. This compromised group exhibits an elevated fasting blood glucose level of at least 125 mg/dL.

Patients amenable to the treatment receive daily oral doses of TLQP-21 polypeptide at a rate of 5 mg/Kg. The progress of these patients is compared to that of a control group that receives only placebo in addition to their doctor recommended therapy.

The TLQP-21 polypeptide is expected to modulate the blood glucose concentration of the patients. Patients administered with the TLPQ-21 poly are expected show improvements in chronic and acute glycemic control, exhibiting lower blood glucose concentrations postprandially and after fasting.

Example 9

Clinical Lab Testing

Clinical lab tests will use a cohort of patients identified as being pre-diabetic. This compromised group exhibits an elevated fasting blood glucose level of at least 100 mg/dL.

Patients amenable to the treatment receive daily oral doses of TLQP-21 peptide at a rate of 5 mg/Kg. The progress of these patients is compared to that of a control group that receives only placebo in addition to their doctor recommended therapy.

The TLQP-21 polypeptide is expected to modulate the blood glucose concentration of the patients. Patients administered with the TLPQ-21 poly are expected show improvements in chronic and acute glycemic control, exhibiting lower blood glucose concentrations postprandially and after fasting.

LISTING OF SEQUENCES

SEQ ID NO:1 is human VGF polypeptide
SEQ ID NO:2 is human VGF polynucleotide (coding sequence from positions 200 to 2047)
SEQ ID NO:3 is rat VGF polypeptide
SEQ ID NO:4 is rat VGF polynucleotide (coding sequence from positions 318 to 2171)
SEQ ID NO:5 is TLQPP
SEQ ID NO:6 is RRRH
SEQ ID NO:7 is HHALPP
SEQ ID NO:8 is human TLQP-21 polypeptide
SEQ ID NO:9 is rat TLQP-21 polypeptide
SEQ ID NO:10 is human TLQP-30 polypeptide
SEQ ID NO:11 is rat TLQP-30 polypeptide
SEQ ID NO:12 is human TLQP-42 polypeptide
SEQ ID NO:13 is rat TLQP-42 polypeptide
SEQ ID NO:14 is rat AQEE-30 polypeptide
SEQ ID NO:15 is rat HHPD-11 polypeptide

---

We claim:

1. A method of treating hyperglycemia comprising peripherally administering to a patient in need of the treatment a therapeutically effective amount of a composition comprising a TLQP-21 biomolecule peptide.

2. The method of claim 1, wherein the patient has Type II diabetes.

3. The method of claim 1, wherein the patient produces insulin.

4. The method of claim 1, wherein the patient is resistant to the effects of insulin.

5. The method of claim 1, wherein the TLQP-21 biomolecule is a peptide from 21 to about 60 amino acids long.

6. The method of claim 1, further comprising administering metformin, a thiazolidinedione or a combination thereof.

7. The method of claim 1, wherein the TLQP-21 biomolecule is a polypeptide administered in an amount of at least about 0.01 mg/kg/day and less than about 150 mg/kg/day.

8. A method for reducing the blood glucose concentration in a mammal comprising peripherally administering to the mammal a therapeutically effective amount of a composition comprising a TLQP-21 biomolecule peptide, wherein the mammal has a fasting blood glucose level of at least about 90 mg/dL.

9. The method of claim 1, wherein the peripheral administration is selected from the group consisting of nasal administration, oral administration, topical administration, cutaneous injection, subcutaneous injection, intramuscular injection, intravenous injection, intradermal injection, and intraperitoneal injection.

10. The method of claim 8, wherein the peripheral administration is selected from the group consisting of nasal administration, oral administration, topical administration, cutaneous injection, subcutaneous injection, intramuscular injection, intravenous injection, intradermal injection, and intraperitoneal injection.

11. The method of claim 1, wherein the peripheral administration is effected in one or more doses throughout a treatment.

12. The method of claim 8, wherein the peripheral administration is effected in one or more doses throughout a treatment.

13. The method of claim 1, wherein the TLQP-21 biomolecule peptide is in a sustained release composition.

14. The method of claim 8, wherein the TLQP-21 biomolecule peptide is in a sustained release composition.

* * * * *